(12) United States Patent
Takizawa et al.

(10) Patent No.: US 8,349,347 B2
(45) Date of Patent: *Jan. 8, 2013

(54) CAPSULE MEDICATION ADMINISTRATION SYSTEM AND MEDICATION ADMINISTRATION METHOD

(75) Inventors: Hironobu Takizawa, Tokyo (JP); Akio Uchiyama, Yokohama (JP); Hidetake Segawa, Tokyo (JP); Masahiro Takata, Tokyo (JP); Hideki Koyanagi, Tokyo (JP)

(73) Assignee: Olympus Corporation, Tokyo (JP)

( * ) Notice: Subject to any disclaimer, the term of this patent is extended or adjusted under 35 U.S.C. 154(b) by 1318 days.

This patent is subject to a terminal disclaimer.

(21) Appl. No.: 12/024,315

(22) Filed: Feb. 1, 2008

(65) Prior Publication Data

US 2008/0131502 A1    Jun. 5, 2008

Related U.S. Application Data

(63) Continuation of application No. 10/951,471, filed on Sep. 28, 2004, now abandoned.

(30) Foreign Application Priority Data

Oct. 1, 2003   (JP) .................................. 2003-343199

(51) Int. Cl.
*A61K 9/48* (2006.01)

(52) U.S. Cl. ........ 424/423; 424/422; 424/426; 424/451; 424/457

(58) Field of Classification Search ............ 424/464–489
See application file for complete search history.

(56) References Cited

U.S. PATENT DOCUMENTS

| | | | |
|---|---|---|---|
| 5,279,607 A | 1/1994 | Schentag et al. | |
| 5,604,531 A | 2/1997 | Iddan et al. | |
| 5,637,594 A | 6/1997 | Poltera | |
| 5,667,331 A | 9/1997 | Lindenthal | |

FOREIGN PATENT DOCUMENTS

| | | |
|---|---|---|
| JP | 6-23020 | 2/1994 |
| JP | 2000-506410 | 5/2000 |
| JP | 2003-38424 | 2/2003 |
| JP | 2003-524448 | 8/2003 |
| WO | WO 92/21307 | 12/1992 |
| WO | WO 9221307 A1 * | 12/1992 |
| WO | WO 97/33513 | 9/1997 |
| WO | WO 00/22975 | 4/2000 |
| WO | WO 0022975 A1 * | 4/2000 |
| WO | WO 02/39112 A2 | 5/2002 |

OTHER PUBLICATIONS

Japanese Office Action dated Feb. 16, 2010 with an English Translation.

* cited by examiner

*Primary Examiner* — Michael G Hartley
*Assistant Examiner* — Micah-Paul Young
(74) *Attorney, Agent, or Firm* — Scully Scott Murphy & Presser, PC

(57) ABSTRACT

A capsule medication administration system includes: a first capsule for internal body marking; a second capsule for medication; a marking device which makes a marking within a living body; a drug retention section which retains a drug; a release device which releases the drug; a detection device which detects the marking; a decision device which decides whether or not a marking which has been detected by the detection device is a specified marking; and a release control device which operates the release device, if it has been decided by the decision device that it is the specified marking; wherein the first capsule comprises the marking device. The second capsule comprises the drug retention section and the release device.

14 Claims, 10 Drawing Sheets

CAPSULE MEDICATION ADMINISTRATION SYSTEM AND MEDICATION ADMINISTRATION METHOD

This application is a continuation of U.S. patent application Ser. No. 10/951,471 filed on Sep. 28, 2004, which claims the priority of Japanese Patent Application 2003-343199 which was filed on Oct. 1, 2003, the contents of each of which are incorporated herein by reference.

BACKGROUND OF THE INVENTION

1. Field of the Invention

The present invention relates to a capsule medication administration system which is ingested into a living body and which performs medication for a diseased part such as a superficial disorder of the digestive organs or the like, and to a capsule medication administration method.

The present invention claims the priority of Japanese Patent Application 2003-343199 which was filed on 1 Oct. 2003, and incorporates its contents herein.

2. Description of Related Art

Nowadays, as means for administering a drug to a patient more safely and also more effectively, attention is being directed towards drug delivery systems (DDS: Drug Delivery System). Such a drug delivery system is a system which uses a drug more effectively by regulating the biological activity of the medicament and its side effects, targeting the diseased part, controlling the release of the drug (controlled release), improving the absorption of the drug, regulating the chemical stability and the metabolic activity and so on of the drug, and causing the drug to act upon a superficial disorder within the living body in the required amount and for just the required period of time. With such a drug delivery system, the technique for taking advantage of it is different according to the type of the disorder; for example, if the superficial disorder which is a diseased part is a malignant tumor, a technique is obtained of targeting and controlled release and the like.

On the other hand, as a device for checking upon the state of health of a patient easily, there is a known capsule type medical device which is orally ingested to within the living body. With this kind of capsule type medical device, various types of information may be provided; for example, it is known to take photographs at random of various parts within the living body, to take samples or the like from within the living body, to release a drug, and the like. As one such device, there is known a capsule endoscope which can form an image after releasing a foaming agent at a predetermined position (the large intestine) within the living body and distending the laminar portion within his body (for example, refer to paragraph 0006 through paragraph 0049 and to FIG. 1 trough FIG. 5 of Japanese Unexamined Patent Application, First Publication No. 2003-38424).

The above described capsule endoscope is provided with a capsule shaped body which has a hemispherical shaped transparent member at its one end surface and a hemispherical mesh member at its other end surface. Within the transparent member there are provided a LED which emits light for illumination to the interior of the living body, and an image formation optical system which forms an image of the interior of the living body. Furthermore, a pH sensor is provided to the capsule body so as to be exposed at its outer surface. The pH value which has been detected by this pH sensor is sent to a control processing circuit, and, when it has been decided from the change of the pH value that the capsule has arrived at the large intestine, this is transmitted from a transmission antenna towards the outside of the living body. Furthermore, as well, the image data which has been formed into an image by the above described image formation optical system is transmitted from the transmission antenna towards the outside of the living body, after having been subjected to predetermined processing. Moreover, a plurality of micro capsules are housed on the inside of the mesh member, and are broken down by emission of ultrasound, and a foaming agent is stored in the insides of these micro capsules which generates a gas by reaction with water.

When a check is to be performed by using this capsule endoscope, the patient first swallows the capsule endoscope so as to ingest it to within his body. The capsule endoscope which has been ingested to within the living body moves within his digestive organs while detecting the pH value within his body by using the pH sensor. When the capsule endoscope arrives at the large intestine, the control processing circuit decides, based upon change of the pH value which has been detected by the pH sensor, that the capsule endoscope has arrived at the large intestine, and issues a notification to that effect to the exterior of the living body from the transmission antenna. When this signal which has been transmitted is received by a receiver or the like on the outside of the living body, the medical staff emit an ultrasonic wave towards the living body using an ultrasonic wave generator. When the ultrasonic wave is emitted, it breaks down the micro capsules, and the foaming agent inside them is released within the large intestine through the mesh member. The foaming agent which has been released within the large intestine reacts with the water component within the large intestine and generates gas, thus distending the large intestine. By the large intestine being distended, it becomes possible to form an image using the image formation optical system over a wide range of the interior of the large intestine which has thus been distended.

In this manner, the above described capsule endoscope is one with is equipped with the function of releasing the foaming agent from the micro capsules at a predetermined position (the large intestine) in the living body, as described above, i.e. with the functions of targeting and controlled release. In particular, new attention is being paid to this kind of capsule type medical device as one means for implementing the above described drug delivery system, since it can simply and conveniently be ingested to the interior of the living body.

SUMMARY OF THE INVENTION

The present invention proposes a capsule medication administration system, including: a first capsule for internal body marking which is orally ingested to within a living body; a second capsule for medication which is also orally ingested to within the living body; a marking device which makes a marking within the living body; a drug retention section which retains a drug; a release device which releases the drug; a detection device which detects the marking; a decision device which decides whether or not a marking which has been detected by the detection device is a specified marking; and a release control device which operates the release device, if it has been decided by the decision device that it is the specified marking; wherein: the first capsule includes the marking device; and the second capsule includes the drug retention section and the release device.

With the capsule medication administration system of the present invention, it is preferable that the second capsule to include the detection device, the decision device, and the release control device.

With the capsule medication administration system of the present invention, it is preferable that the first capsule to include: an acquisition device which acquires in-vivo information; a medication determination device which, based upon the in-vivo information which has been acquired by the acquisition device, determines whether or not to perform medication for a site which is indicated in the in-vivo information; and a specification device which, based upon the determination by the medical determination device, specifies a marking which indicates a site to perform medication, from among the markings which have been made within the living body; and for the decision device to decide whether or not a marking which has been detected by the detection device is the marking which has been specified by the specification device.

With the capsule medication administration system of the present invention, it is preferable that the first capsule to include a first memory which establishes a correspondence between the positions of the markings and the in-vivo information and stores them; and for the second capsule to include a second memory which stores information about the marking which has been specified by the specification device.

With the capsule medication administration system of the present invention, it is preferable that there to be further included a unit external to the living body, disposed outside the living body; and for: the first capsule to include an acquisition device which acquires in-vivo information while establishing a correspondence with the positions of the markings, and a first capsule transmission device which transmits the in-vivo information which has been acquired by the acquisition device towards the unit external to the living body; and for the unit external to the living body to include: a reception device external to the living body which receives the in-vivo information which has been transmitted from the first capsule transmission device; a medication determination device which, based upon the in-vivo information which has been acquired by the acquisition device, determines whether or not to perform medication for a site which is indicated in the in-vivo information; and a specification device which, based upon the determination by the medication determination device, specifies a marking, from among the markings which have been made within the living body, which indicates a site to perform medication.

With the capsule medication administration system of the present invention, it is preferable that there to be further included a unit external to the living body, disposed outside the living body; and: for the first capsule to include an acquisition device which acquires in-vivo information while establishing a correspondence with the positions of the markings; for the second capsule to include: the detection device; a second capsule transmission device which transmits information about the markings which have been detected by the detection device towards the unit external to the living body; a second capsule reception device which receives a control signal for causing the release device to operate; and the release control device; for the unit external to the living body to include: a reception device external to the living body which receives the information about markings which has been transmitted from the second capsule transmission device; the decision device; and a transmission device external to the living body which, if it has been decided by the decision device that it is the specified marking, transmits the control signal towards the second capsule reception device; for the decision device to decide whether or not information about a marking which has been received by the reception device external to the living body is the specified marking; and for the release control device to cause the release device to operate, when the control signal has been received by the second capsule reception device.

With the capsule medication administration system of the present invention, it is preferable that the first capsule to include a first capsule transmission device which transmits the in-vivo information which has been acquired by the acquisition device towards the unit external to the living body; for the unit external to the living body to include: a medication determination device which, based upon the in-vivo information which has been acquired by the acquisition device, determines whether or not to perform medication for a site which is indicated by the in-vivo information; and a specification device which, based upon the determination by the medication determination device, specifies a marking which indicates the side at which medication is to be performed from among the markings which have been made within the living body; and for the reception device external to the living body to receive the in-vivo information which has been transmitted from the first capsule transmission device.

The present invention proposes a capsule medication administration system, including: a first capsule for internal body marking which is orally ingested to within a living body; a second capsule for medication which is also orally ingested to within the living body; a third capsule for long time period marking which is also orally ingested to within the living body; a marking device which makes a marking within the living body; a long time period marking device which makes, within the living body, a long time period marking which can last for a longer time period than the marking; a drug retention section which retains a drug; a release device which releases the drug; a detection device which detects the marking; a decision device which decides whether or not a marking which has been detected by the detection device is a specified marking; a long time period marking control device which operates the long time period marking device, if it has been decided by the decision device that it is the specified marking; a long time period marking detection device which detects the long time period marking; and a release control device which operates the release device, if the long time period marking has been decided by the long time period marking detection device; wherein: the first capsule includes the marking device; the second capsule includes the drug retention section which retains the drug, and the release device which releases the drug; and the third capsule includes the long time period marking device.

With the capsule medication administration system of the present invention, it is preferable that the third capsule to include the detection device, the decision device, and the long time period marking control device.

With the capsule medication administration system of the present invention, it is preferable that the second capsule to include the long time period marking detection device and the release control device.

With the capsule medication administration system of the present invention, it is preferable that the first capsule to include: an acquisition device which acquires in-vivo information; a medication determination device which, based upon the in-vivo information which has been acquired by the acquisition device, determines whether or not to perform medication for a site which is indicated in the in-vivo information; and a specification device which, based upon the determination by the medical determination device, specifies a marking which indicates a site to perform medication, from among the markings which have been made within the living body.

With the capsule medication administration system of the present invention, it is preferable that the first capsule to include a first memory which establishes a correspondence between the positions of the markings and the in-vivo information and stores them; and for the medication determination device to determine whether or not to perform medication for a site which is indicated in the in-vivo information, based upon the in-vivo information which has been stored in the first memory.

With the capsule medication administration system of the present invention, it is preferable that the third capsule to include a second memory which stores the marking which has been specified by the specification device; and for the decision device to make a decision as to whether or not a marking which has been detected by the detection device is the specified marking which has been stored in the second memory.

With the capsule medication administration system of the present invention, it is preferable that there to be further included a unit external to the living body, disposed outside the living body; and: for the first capsule to include an acquisition device which acquires in-vivo information while establishing a correspondence with the positions of the markings, and a first capsule transmission device which transmits the in-vivo information which has been acquired by the acquisition device towards the unit external to the living body; and for the unit external to the living body to include: a reception device external to the living body which receives the in-vivo information which has been transmitted from the first capsule transmission device; a medication determination device which, based upon the in-vivo information which has been acquired by the acquisition device, determines whether or not to perform medication for a site which is indicated in the in-vivo information; and a specification device which, based upon the determination by the medication determination device, specifies a marking, from among the markings which have been made within the living body, which indicates a site to perform medication.

With the capsule medication administration system of the present invention, it is preferable that there to be further included a unit external to the living body, disposed outside the living body; and: for the first capsule to include an acquisition device which acquires in-vivo information while establishing a correspondence with the positions of the markings; for the third capsule to include: the detection device; a third capsule transmission device which transmits information about the markings which have been detected by the detection device towards the unit external to the living body; and a third capsule reception device which receives a control signal for causing the long time period marking device to operate; and the long time period marking control device; for the unit external to the living body to include: a reception device external to the living body which receives the information about markings which has been transmitted from the third capsule transmission device; a decision device which decides whether or not information about a marking which has been received by the reception device external to the living body is a specified marking; and a transmission device external to the living body which, if it has been decided by the decision device that it is the specified marking, transmits the control signal towards the third capsule reception device; and for the long time period marking control device to cause the long time period marking device to operate, if the control signal has been received by the third capsule reception device.

With the capsule medication administration system of the present invention, it is preferable that the second capsule to include the long time period marking detection device and the release control device.

With the capsule medication administration system of the present invention, it is preferable that there to be further included a unit external to the living body, disposed outside the living body; and wherein: for the second capsule to include: the long time period marking detection device; a second capsule transmission device which transmits information about the long time period marking which has been detected by the long time period marking detection device towards the unit external to the living body; and a second capsule reception device which receives a control signal for causing the release device to operate; for the unit external to the living body to include: a reception device external to the living body which receives the information about the long time period marking which has been transmitted from the second capsule transmission device; and a transmission device external to the living body which, if information about the long time period marking has been received by the reception device external to the living body, transmits the control signal towards the second capsule reception device; and for the release control device to cause the release device to operate, when the control signal has been received by the second capsule reception device.

The present invention proposes a capsule medication administration system, including: a first capsule for acquiring in-vivo information, which is orally ingested to within the living body; a second capsule for medication which is also orally ingested to within the living body; a third capsule for long time period marking which is also orally ingested to within the living body; and a unit external to the living body which is disposed outside the living body; and wherein: the first capsule includes: a marking device which makes a marking within the living body; and an acquisition device which acquires in-vivo information while establishing a correspondence with the positions of the markings; the third capsule includes: a detection device which detects the markings; a third capsule transmission device which transmits information about the markings which have been detected by the detection device towards the unit external to the living body; a long time period marking device which makes, within the living body, a long time period marking which can last for a longer time period than the marking; a third capsule reception device which receives a control signal for causing the long time period marking device to operate; and a long time period marking control device which causes the long time period marking device to operate, if the control signal has been received by the third capsule reception device; the second capsule includes: a drug retention section which retains a drug; a release device which releases the drug; a long time period marking detection device which detects the long time period marking; and a release control device which operates the release device, if the long time period marking has been decided by the long time period marking detection device; and the unit external to the living body includes: a reception device external to the living body which receives the information about the markings which has been transmitted from the third capsule transmission device; a medication determination device which, based upon the in-vivo information which has been acquired by the acquisition device, determines whether or not to perform medication for a site which is indicated in the in-vivo information; a specification device which, based upon the determination by the medication determination device, specifies a marking, from among the markings which have been made within the living body, which indicates the position of a diseased part for which medication must be performed; a decision device which, from the marking which has been specified by the specification device and the information about the markings which has been received by the reception device external to the living body, decides whether or not a marking which has been detected by the detection device is a specified marking; and a transmission device external to the living body, which transmits the control signal towards the third capsule reception device, if it has been decided by the decision device that it is the specified marking.

With the capsule medication administration system of the present invention, it is preferable that the long time period marking device to include a indwell device which deploys a indwelling member within the living body.

With the capsule medication administration system of the present invention, it is preferable that the long time period marking device to include a indwell device which deploys a indwelling member within the living body.

With the capsule medication administration system of the present invention, it is preferable that the first capsule to include a first memory which establishes a correspondence between the positions of the markings and the in-vivo information, and stores it; and for the medication determination device to acquire the in-vivo information from the first memory.

With the capsule medication administration system of the present invention, it is desirable, every time the detection device detects a marking, for the decision device to count the number thereof, and to decide that the marking which is detected by the detection device is the specified marking, when the number of the marking arrives at a specified number.

With the capsule medication administration system of the present invention, it is desirable, every time the detection device detects a marking, for the decision device to count the number thereof, and to decide that the marking which is detected by the detection device is the specified marking, when the number of the marking arrives at a specified number.

With the capsule medication administration system of the present invention, it is preferable that the marking device to include a liquid chemical release device which releases a liquid chemical within the living body.

With the capsule medication administration system of the present invention, it is preferable that the marking device to include a liquid chemical release device which releases a liquid chemical within the living body.

With the capsule medication administration system of the present invention, it is preferable that the acquisition device to include an observation device which includes an imaging device which forms an image of the interior of the living body, and an illumination device which illuminates the interior of the living body.

With the capsule medication administration system of the present invention, it is preferable that the acquisition device to include an observation device which includes an imaging device which forms an image of the interior of the living body, and an illumination device which illuminates the interior of the living body.

With the capsule medication administration system of the present invention, it is preferable that the acquisition device to include a blood sensor which detects hemorrhage within the living body.

With the capsule medication administration system of the present invention, it is preferable that the acquisition device to include a blood sensor which detects hemorrhage within the living body.

The present invention proposes a medication administration method, including: a step of disposing a first capsule which includes an observation device and a marking device within the coelom of a living body; a step of observing the living body with the observation device; a step of making a marking within the living body with the marking device; a step of determining a medication position; a step of determining a specified marking which indicates the medication position; a step of disposing a second capsule which includes a medication device and a marking detection device within the coelom; a step of detecting the marking; a step of deciding whether or not a marking which has been detected is the specified marking; and a step of, if it has been decided that it is the specified marking, releasing a drug by the medication device.

The present invention proposes a medication administration method, including: a step of disposing a first capsule which includes an observation device and a marking device within the coelom of a living body; a step of observing the living body with the observation device; a step of making a marking within the living body with the marking device; a step of determining a medication position within the living body; a step of determining a specified marking which indicates the medication position; a step of disposing a third capsule which includes a long time period marking device within the coelom; a step of detecting the marking; a step of deciding whether or not a marking which has been detected is the specified marking; a step of, if it has been decided that it is the specified marking, making a long time period marking with the long time period marking device; a step of disposing a second capsule which includes a medication device and a long time period marking detection device within the coelom; a step of detecting the long time period marking; and a step of, if a long time period marking which has been detected, releasing a drug by the medication device.

With the medication administration method of the present invention, it is preferable that the step of making a marking with the marking device within the living body to be repeated a plurality of times.

With the medication administration method of the present invention, it is preferable that the step of making a marking with the marking device within the living body to be repeated a plurality of times at equal time intervals.

DETAILED DESCRIPTION OF THE INVENTION

In the following, the first embodiment of the capsule medication administration system according to the present invention will be explained with reference to FIG. 1 through FIG. 10.

Figure 1:
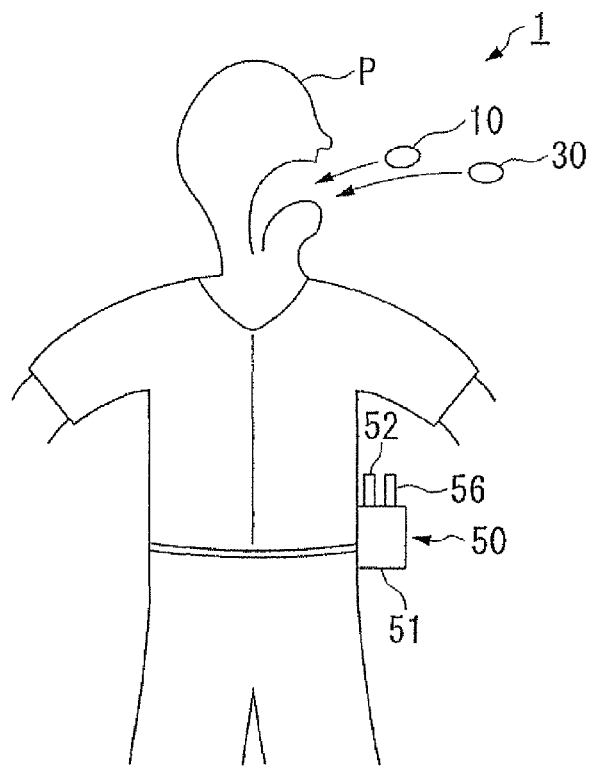
FIG. 1 is a schematic figure showing a first embodiment of the capsule medication administration system according to the present invention.

As shown in FIG. 1, the capsule medication administration system 1 of this embodiment includes a capsule for observation (a first capsule) 10 which is orally ingested into a living body P (i.e. into his living body) for capturing information about his body, a capsule for medication (a second capsule) 30, and a unit 50 external to the living body which is disposed outside the living body.

Figure 2:
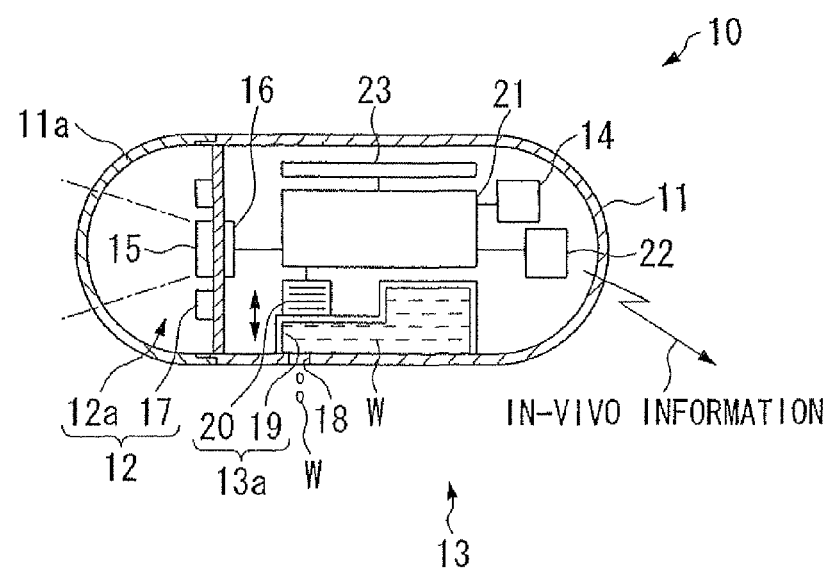
FIG. 2 is a sectional view showing a capsule for observation which is used in the capsule medication administration system shown in FIG. 1.

As shown in FIG. 2, the capsule for observation 10 includes, within a capsule shaped casing 11: an observation device (an acquisition device) 12 which acquires a photographic image, which is in-vivo information, by photographing various internal portions within the living body; a marking device 13 which includes a liquid chemical release device 13a which makes a marking M by releasing a marking material (a liquid chemical) W within the living body; and a memory 14 (a first memory) which stores the positions of the marking M which has been made by the marking device 13 and the photographic image which has been acquired by the observation device 12.

The casing 11 includes a cover 11a which is formed from a plastic material or the like so as tightly to seal its interior, and which is transparent at one end portion thereof. An objective lens 15 for forming images of various internal portions of the living body is disposed in the interior of this transparent cover 11a, and an image formation element 16, such as for example a CMOS imager or a CCD or the like, is disposed at the image focusing position of this objective lens 15. This objective lens 15 and image formation element 16 constitute an imaging device 12a which forms images of the interior of the living body. Furthermore, LEDs (illumination devices) 17 which emit light for illumination so as to illuminate the visual field range of the objective lens 15 are disposed around the perimeter of the objective lens 15. In other words, this imaging device 12a and these LEDs 17 constitute the observation device 12.

Furthermore, a minute discharge aperture 18 is formed at one portion of the casing 11, and at the inside of this discharge aperture 18 there is provided a reservoir 19 which stores a marking material W such as a dye (for example the marking material "SPOT" made by the US company GI Supply or the like), or a fluorescent substance, a magnetic substance, a radioactive substance or the like. A portion of the reservoir 19 is made to be elastically deformable, and a piezo element 20 is provided at its position of elasticity. In other words it is possible, by supplying a voltage signal or the like to the piezo element 20, for the piezo element 20 to expand and press upon the reservoir 19, thus discharging the marking material W from the discharge aperture 18 towards the exterior of the casing 11. By doing this, it is possible to make a marking M such as a black spot upon the luminal wall of the digestive organs or the like within the living body. In other words, this reservoir 19 and piezo element 20 constitute a liquid chemical release device 13a, and the liquid chemical release device 13a and the discharge aperture 18 constitute a marking device 13. It should be understood that, when a predetermined time interval has elapsed after the marking M has been made within the living body, the marking material W is naturally metabolized within the living body and disappears.

Furthermore, within the casing 11, there are housed a control processing section 21 which, along with controlling the observation device 12 and the liquid chemical release device 13a, also performs predetermined processing upon the in-vivo information which has been acquired by the observation device 12 and sends it to a memory 14, a transmission device (the first capsule transmission device) 22 which consists of a transmitter which wireless transmits the in-vivo information and the like which is stored in the memory 14 towards the unit 50 external to the living body and a transmission antenna, and a battery 23 which supplies electrical power to the various structural components described above.

The control processing section 21 is equipped with the function of, after ingestion to within the living body, sending a signal to the piezo element 20 so as to operate the liquid chemical release device 13a, so as to make a marking M within the living body periodically, for example once every five minutes, while moving within the living body. Furthermore it is equipped with the function of, at the same time, controlling the observation device 12 so as randomly to form images of the interior of the living body, for example twice every second, thus causing it to acquire in-vivo information. Moreover, along with performing predetermined processing upon the in-vivo information which has been sent from the observation device 12, the control processing section 21 also establishes a correspondence between this in-vivo information and the operational timing of the piezo element 20, and stores it in succession in the memory 14. In other words, it is equipped with the function of establishing a correspondence between the positions of the markings M which have been made within the living body and the in-vivo information, and of storing it in the memory 14. Furthermore, as described above, it is also capable of transmitting it from the memory 14 via the transmission device 22 to the unit 50 external to the living body. Moreover, it is also capable of transmitting the in-vivo information which it has acquired directly in order towards the unit 50 external to the living body, i.e. not via the memory 14.

Figure 3:
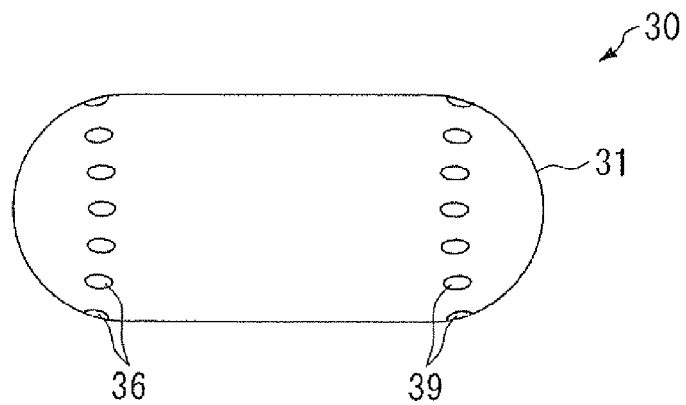
FIG. 3 is an external view showing a capsule for medication which is used in the capsule medication administration system shown in FIG. 1.
Figure 4:
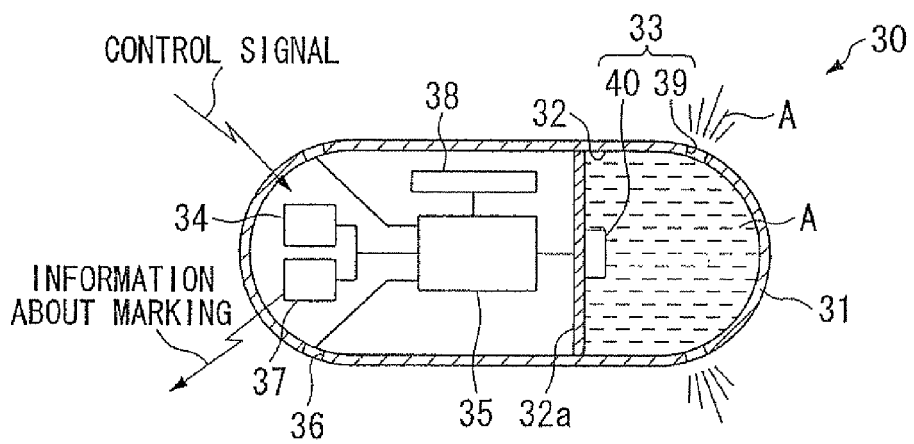
FIG. 4 is a sectional view showing the capsule for medication shown in FIG. 3.

As shown in FIG. 3 and FIG. 4, the capsule for medication 30 includes, within a capsule shaped casing 31: a reservoir (a drug retention section) 32 which retains a drug A in liquid form; a release device 33 which releases the drug A which has been retained in the reservoir 32; a reception antenna (a second capsule reception device) 34 which receives a control signal which has been transmitted from the unit 50 external to the living body; a control section (a release control device) 35 which causes the release device 33 to operate when a control signal has been received by the reception antenna 34; sensors (detection devices) 36 which detect a marking M that has been made within the living body; a transmission antenna (a second capsule transmission device) 37 which transmits information about a marking M which has been detected by the sensors 36 to the unit 50 external to the living body; and a battery 38 which supplies electrical power to the various structural components.

The casing 31 is made from a plastic material or the like so as tightly to seal its interior, and the reservoir 32 is provided at the interior portion of its one end so as to be surrounded by a wall portion 32a and the inner peripheral surface of the casing 31. On the outer surface of the casing 31, which is the perimeter of the reservoir 32, there are formed a plurality of drug apertures 39 around the axis of the casing 31. Thin membranes are formed upon the drug apertures 39, so that the drug A which is retained in the reservoir 32 does not leak out from the drug apertures 39. Furthermore, a heater 40 is provided within the reservoir 32. The heater 40 is equipped with the function of causing gas bubbles to be generated by instantaneous heating, so that the thin membranes of the drug apertures 39 may be broken by the pressure thereof and the drug A may be released from the drug apertures 39. In other words, these drug apertures 39 and this heater 40 constitute a release device 33.

A plurality of the sensors 36 are formed around the axis of the casing 31 upon the outer surface of its other end. The sensors 36 are equipped with the function of detecting a marking M which has been made by the capsule for observation 10 during its moving within the living body, and sending it to the control section 35. Furthermore, when the control section 35 receives a control signal which has been sent from the unit 50 external to the living body via the reception antenna 34, it controls the heater 40 so as to cause it to heat up.

Furthermore, if for example the marking material W is a dye or a fluorescent substance of a specified color, then the sensors 36 consist of optical sensors which have sensitivity to the wavelength of that color, and of LEDs for illuminating the interior of the lumen. These LEDs are optimized for a wavelength which is matched to the characteristics of the marking material W.

Figure 5:
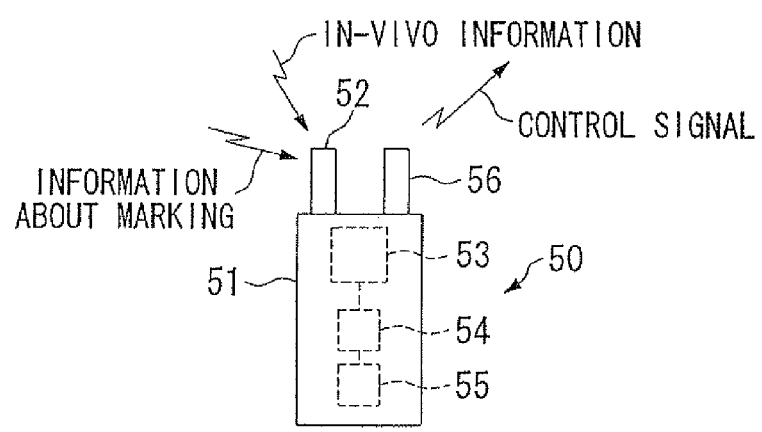
FIG. 5 is a structural view of a unit external to the living body which is used in the capsule medication administration system shown in FIG. 1.

As shown in FIG. 1 and FIG. 5, the unit 50 external to the living body includes, within a main body 51 which can be put on to the outside of the patient P: a reception antenna (a reception device external to the living body) 52 which receives information about a marking M which has been sent from the transmission antenna of the capsule for medication 30; a determination section (a medication determination device) 53 which determines, based upon the in-vivo information which has been stored in the memory 14 of the capsule for observation 10, whether or not medication is required for a diseased part X which is shown in the in-vivo information; a specification section (a specification device) 54 which specifies a marking M which gives the position of a diseased part X based upon the determination by the determination section 53; a decision section (a decision device) 55 which, from information about a marking M which has been specified by the specification section 54 and information about a marking M which has been received by the reception antenna 52, decides whether or not the marking M which has been detected is the specified marking M; and a transmission antenna (a transmission device external to the living body) 56 which transmits a control signal towards the capsule for medication 30 when it has been decided by the decision section 55 that it is the specified marking M.

The main body 51 can be put on to the exterior of the living body by being put onto a belt or the like of the patient P. The reception antenna 52 and the transmission antenna 56 are provided, for example, so as to project from this main body 51. Furthermore, the reception antenna 52 is equipped with the function of receiving the information about the markings M from the capsule for medication 30, and the in-vivo information which has been put into correspondence with the markings M sent and arrived from the transmission device 22 of the capsule for observation 10. Moreover, the reception antenna 52 is equipped with the function of transmitting the in-vivo information and so on which it has received to the determination section 53 and the specification section 54.

Along with detecting, for example, red color from the photographic image which has been sent from the memory 14 via the reception antenna 52, which is in-vivo information, the determination section 53 compares together this detected amount and a threshold value which is set in advance, and, if the result of this comparison is greater than or equal to a threshold value, determines that it is a hemorrhagic site (a diseased part X) for which medication is required.

Furthermore, the specification section 54 specifies the marking M which designates the position of the diseased part X from the in-vivo information which specifies the diseased part X which has been determined by the determination section 53 and the marking M which has been established in correspondence with the in-vivo information which has been sent from the memory 14 and has arrived via the reception antenna 52. At this time, the specified marking M is specified by the number in sequence of the marking M from the oral ingestion, for example, as the tenth marking M.

Moreover, when it receives the information about a marking M which has been sent from the capsule for medication 30 and has arrived, the reception antenna 52 sends it to the decision section 55. The decision section 55 compares together the information about the marking M which has been sent and has arrived, and the marking M which designates the position of the diseased part X which has been specified by the specification section 54, and makes a decision as to whether or not the marking M which has been detected by the capsule for medication 30 is the specified marking M. At this time, the decision section 55 decides whether or not it is the specified marking M by counting the number of the markings M which have been sent from the capsule for medication 30. If it decides that the marking M which has been detected by the capsule for medication 30 is the specified marking M, in other words that medication is required, then it dispatches a control signal from the transmission antenna 56.

The case of administration of medication with a drug A to a diseased part X within the living body P by the capsule medication administration system 1 with this type of structure will be described below with reference to FIG. 6 through FIG. 10.

Figure 6:
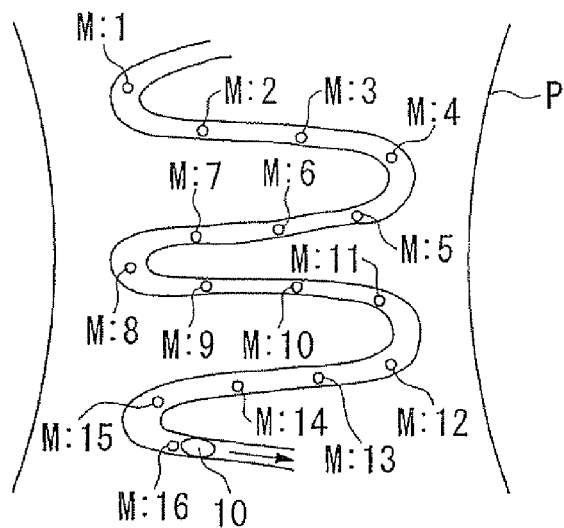
FIG. 6 is a figure showing a situation in which markings are being made by the capsule for observation within a living body.

First, as shown in FIG. 1, in a medical facility or the like such as a hospital or the like, the patient P puts on the unit 50 external to the living body. After putting this on, upon the command of a physician, he swallows and orally ingests (S1) the capsule for observation 10. At this time, a switch not shown in the drawings in the capsule for observation 10 is turned on when it is ingested, so that electrical power is supplied from the battery 23 and the control processing section 21 starts to operate. As shown in FIG. 6, while the capsule for observation 10 which has been orally ingested moves within the living body A, the control processing section 21 causes the liquid chemical release device 13a to operate, and thereby markings M are made upon the luminal wall of the digestive organs within the living body, for example at the rate of one every five minutes. In other words, the control processing section 21 sends an operating signal or the like to the piezo element 20 to expand it. Due to this, pressure is applied to the reservoir 19, which expels the marking material W from the discharge aperture 18, thus making the markings M. Furthermore, at the same time, the control processing section 21 causes the observation device 12 to operate, and thereby acquires in-vivo information (S2) by forming images of the various internal parts thereof; for example at a rate of two per second. Moreover, the control processing section 21 establishes a correspondence between this in-vivo information which has been acquired by the observation device 12 and the positions of the markings M, and, stores it this in the memory 14, wirelessly transmits it from the transmission device 22 to the unit 50 external to the living body (S3). This in-vivo information which has been transmitted is received by the reception antenna 52 of the unit 50 external to the living body, and is sent to the determination section 53 and to the specification section 54.

On the other hand, when the determination section 53 of the unit 50 external to the living body acquires a photographic image, which is in-vivo information, via the reception antenna 52, it makes a decision as to whether or not medication is necessary for a diseased part which is shown in that photographic image. For example, along with detecting only red color from the photographic image, it may compare together the detected amount thereof and a threshold value which is set in advance, and, if the result of this comparison is that the detected amount is greater than or equal to the threshold value, then it may decide that this is a hemorrhagic site, in other words a diseased part X, for which medication is required (S4).

Furthermore, when this decision is made, the specification section 54 specifies the marling M that indicates the position of the diseased part X (S5). In other words, since the in-vivo information and the positions of the markings M are sent via the reception antenna 52 to the specification section 54 with a correspondence being established between them, the specification of the marking M which is related to the in-vivo information may be performed from the in-vivo information of the diseased part X which has been determined by the determination section 53. It should be understood that, at this time, the specified marking M is specified by the number in order of the marking M, i.e. by which numbered marking M it is.

Figure 7:
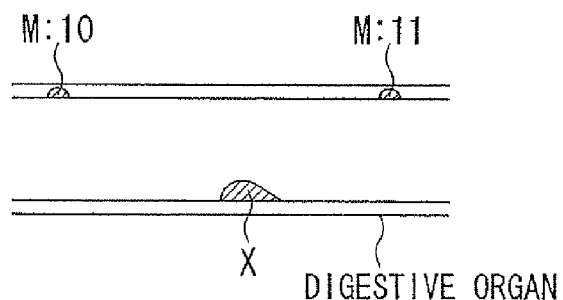
FIG. 7 is a figure showing a situation in which a diseased part is positioned between a tenth marking and an eleventh marking.

It should be understood that, in this embodiment, as shown in FIG. 7, the position of the diseased part X is supposed as being positioned between the tenth marking M and the eleventh marking M, so that the specified marking M which indicates the position of the diseased part X is taken as being the tenth marking.

On the other hand, after the observation by the capsule for observation 10 has terminated by a predetermined time period having elapses from when the patient P orally ingested the capsule for observation 10, or by excretion of the capsule for observation 10 or the like, the capsule for medication 30 is orally ingested (S6) according to a medication time which has been determined. It should be understood that the patient P may leave the medical facility or the like after having been given the capsule for medication 30 by a physician or the like.

After this, while the capsule for medication 30 which has been orally ingested by the patient P moves within the living body, the markings M which have been made by the capsule for observation 10 are detected by the sensors 36 (S7). When a sensor 36 detects a marking M, information about this marking M is transmitted to the control section 35, and the control section 35 wirelessly transmits it from the transmission antenna 37 to the unit 50 external to the living body (S8).

The information about the markings M that has been transmitted is received by the reception antenna 52 of the unit 50 external to the living body, and is sent to the decision section 55. By counting the number of the markings M which are transmitted, the decision section 55 decides whether or not this is the marking M which specifies the position of the diseased part X which has been specified by the specification section 54 (S9). In other words, since the specified marking is the tenth marking M, it is decided that the marking M which is initially detected is not the specified marking M. Furthermore, since the marking M which is next transmitted is the second marking M according to count number, it is decided that it is not the specified marking M.

Thus, when the capsule for medication 30 has detected the tenth marking M, the decision section 55 of the unit 50 external to the living body decides according to the count number that this marking M which has been sent is the tenth marking M, in other words, that it is the specified marking M for which medication is required (S10).

Figure 8:
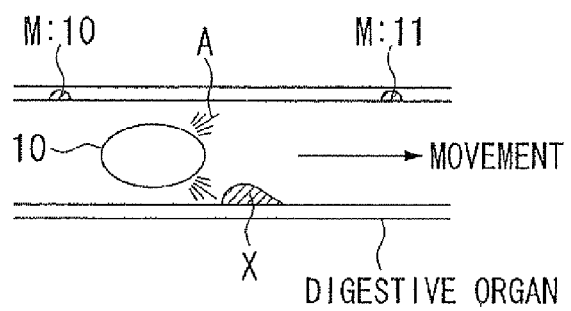
FIG. 8 is a figure showing a situation in which the capsule for medication detects a tenth marking (a specified marking) and a drug is released.
Figure 9:
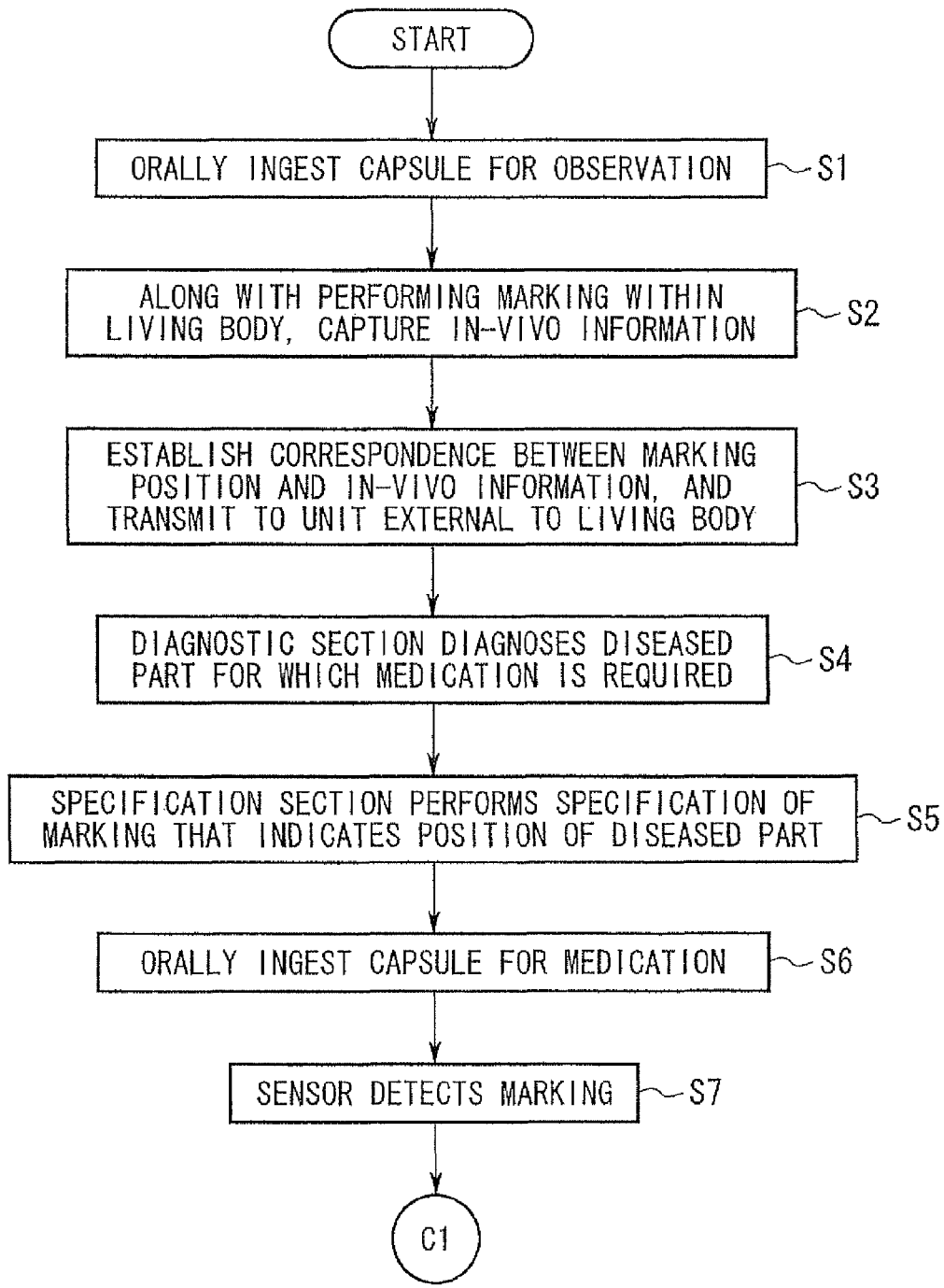
FIG. 9 is a flow chart for when medication is performed for a diseased part by the capsule medication administration system.
Figure 10:
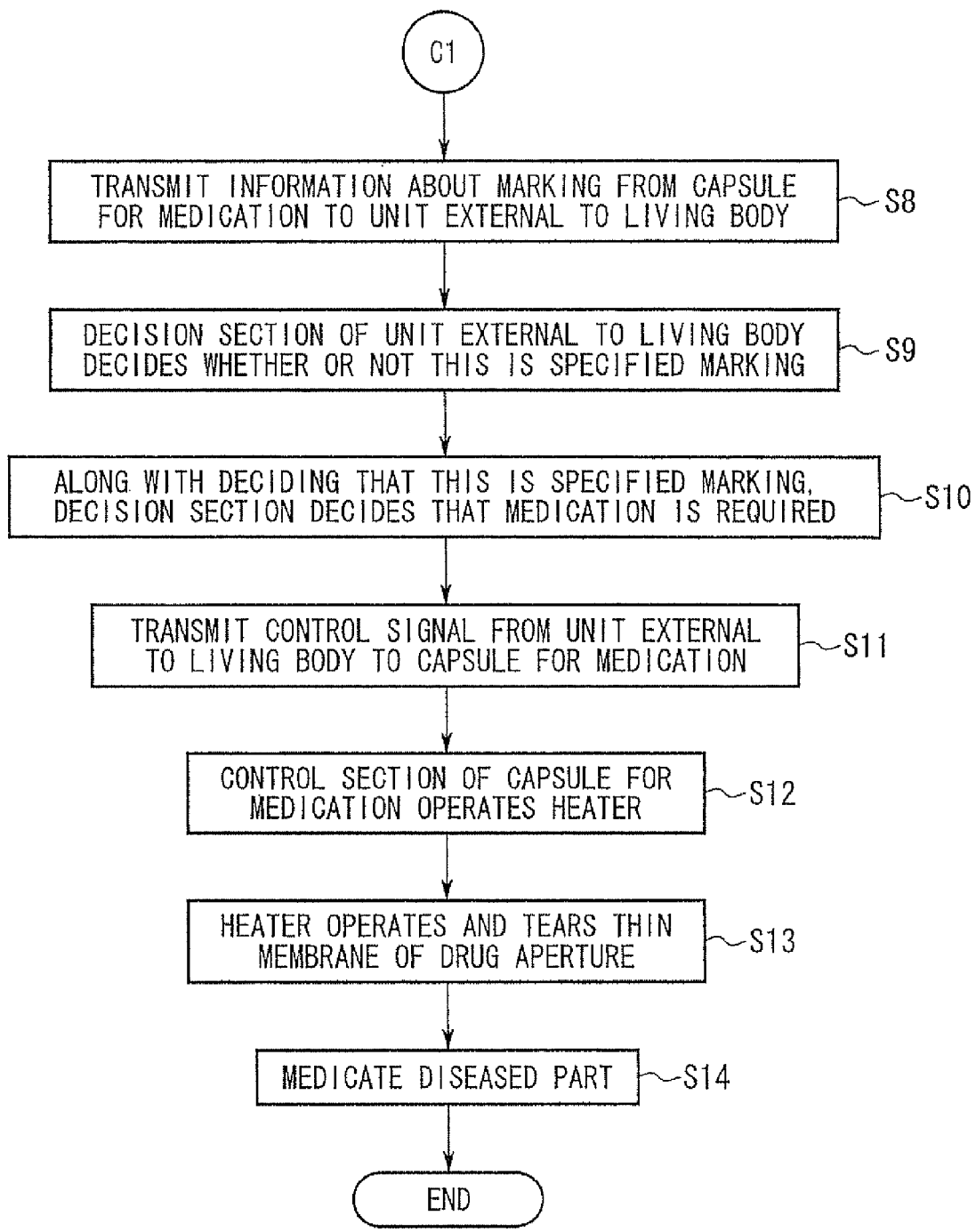
FIG. 10 is a flow chart which continues on from the flow chart of FIG. 9.

When it is decided that medication is required, the decision section 55 wirelessly transmits a control signal from the transmission antenna 56 towards the capsule for medication 30 (S11). The control signal which has been transmitted is received by the reception antenna 34 of the capsule for medication 30, and is transmitted to the control section 35. The control section 35 receives this control signal and operates the heater 40 (S12). Due to this, the heater 40 applies heat momentarily and generates gas bubbles, and due to the pressure of these gas bubbles the thin membranes of the drug apertures 39 are broken (S13), and, as shown in FIG. 8, the drug A within the reservoir 32 is released from the drug apertures 39 to the exterior of the casing 11. In other words, since the position of the diseased part X is indicated by the specified marking M, the drug which has been released comes to act directly upon the diseased part X. Due to this, it is possible to perform medication directly upon the diseased part X (S14).

According to the capsule medication administration system 1 as described above, acquisition of in-vivo information, which is photographic images of the patient P, is performed by the capsule for observation 10 while it makes the markings M internally to the living body. The unit 50 external to the living body is able to acquire the in-vivo information with a correspondence being established with the positions of the markings M which are stored in the memory 14 by wireless communication with the capsule for observation 10. The determination section 53 of the unit 50 external to the living body determines upon the diseased part X for which medication is required based upon this in-vivo information, and the specification section 54, which receives this decision, performs specification of the marking M which indicates the position of the diseased part X for which medication is required. In other words, it is possible to designate the specified marking M which indicates the position of the diseased part X.

It is possible to release the drug A at the position of the specified marking M by the capsule for medication 30, based upon the decision by the decision section 55 of the unit 50 external to the living body. At this time, since the specified marking M indicates the position of the diseased part X, it is possible for the drug A to act directly upon the diseased part X. In other words, it is possible to medicate the diseased part X reliably. Furthermore, the medication is not performed after detecting the diseased part X; since, rather, the medication is performed by detecting the specified marking M which indicates the position of the diseased part X, accordingly the diseased part X is not passed over while the drug A is being released.

Furthermore, since the decision as to whether or not the medication is required is performed by the unit 50 which is external to the living body, accordingly it is possible to utilize a simple structure for the capsule for observation 10 and for the capsule for medication 30, and it is possible to anticipate a reduction in the size thereof.

Furthermore, the decision as to whether or not this is the specified marking M is performed by the decision section 55 of the unit 50 external to the living body counting the number of the markings M. Thus, since it is done not with the color or the shape or the like of the markings M, but rather by counting the number thereof which are detected, accordingly detection mistakes do not occur, and it is possible to detect the specified marking M easily and moreover with high accuracy, and thus it is possible to perform medication for the diseased part X more accurately. Furthermore, since it is also possible to anticipate, according to the count number of the markings M, that the system is getting near the marking M, accordingly it is possible to detect the specified marking M with high accuracy.

It should be understood that although, in this embodiment, the in-vivo information is acquired with a correspondence being established with the positions of the markings M which are stored in the memory 14 by the unit 50 which is external to the living body performing wireless communication with the capsule for observation 10, this should not be considered as being limitative; for example, it would also be acceptable to arrange for this information to be taken from the memory 14 after retrieving the capsule for observation 10 after it has been excreted. Since, in this case, the transmission device 22 and so on would be unnecessary, accordingly it would be possible to make the capsule for observation 10 with a more simple structure, so that it would be possible to anticipate a further reduction in the size thereof.

Furthermore, although the diseased part X for which medication is required is determined upon by the decision section 55 of the unit 50 external to the living body comparing together the in-vivo information and a threshold value, this should not be considered as being limitative; for example, it would also be acceptable for the determination section 55 to be connected to a personal computer or the like, and for this decision to be delegated to the judgment of a physician. By doing this, it is possible to make this decision more accurately.

Moreover, although the sensors 36 were optical sensors, if an function of optical observation were to be imparted to the capsule for medication 30, it would also be possible to combine an optical observation function and optical sensors. Furthermore, if the marking material W were to be a radioactive substance, radiation detection sensors would be utilized for the sensors 36.

Yet further, it would also be acceptable to provide the liquid chemical release device 13a in a plurality to the capsule for observation 30, to put respectively different marking materials W into them, and to arrange to discharge these marking materials W alternately. Since by doing this the different marking materials W would be detected alternately by the capsule for medication 30, accordingly it would be possible to decided upon the position for medication with greater accuracy, since it would be detected if any oversight in detection had occurred, for example if the spot of a marking M had been omitted, or if the same marking M had been detected twice in succession.

Next, the second embodiment of the capsule medication administration system according to the present invention will be explained with reference to FIG. 11 through FIG. 13. It should be understood that in this second embodiment, to structural elements which are the same as the first embodiment, the same reference symbols are appended, and the explanation thereof is curtailed.

Figure 11:
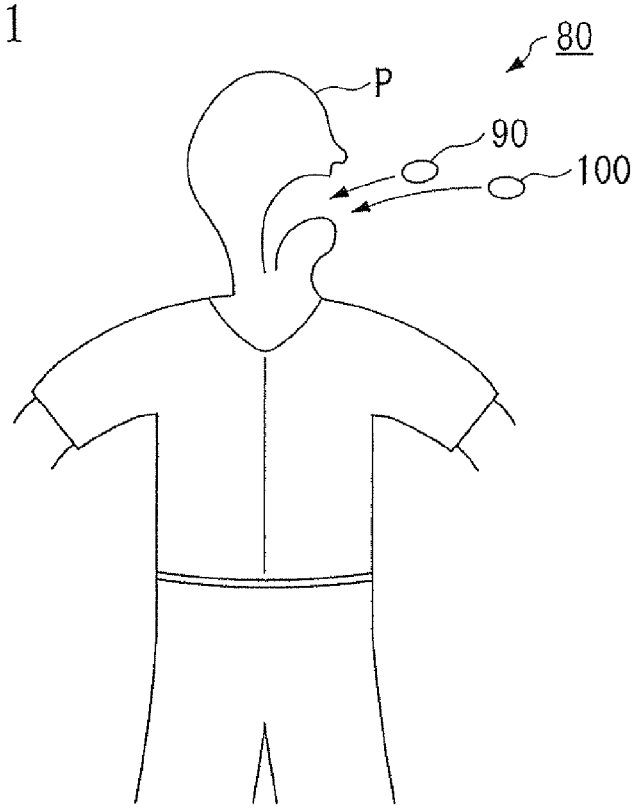
FIG. 11 is a schematic view showing a second embodiment of the capsule medication administration system according to the present invention.

The point in which this second embodiment differs from the first embodiment, is that while, in the first embodiment, in addition to the capsule for observation 10 and the capsule for medication 30, the unit 50 external to the living body was also provided, by contrast, as shown in FIG. 11, the capsule medication administration system 80 of the second embodiment consists of a capsule for observation (a first capsule) 90 and the capsule for medication (a second capsule) 100.

Figure 12:
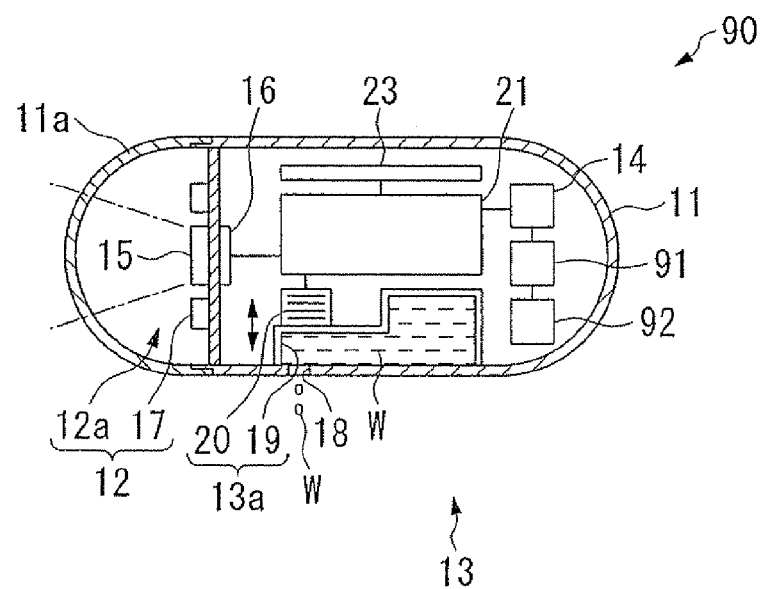
FIG. 12 is a sectional view showing a capsule for observation which is used by the capsule medication administration system shown in FIG. 11.

As shown in FIG. 12, the capsule for observation 90 includes, within a casing 11, a determination section (a medication determination device) 91 which, based upon a photographic image which is stored in the memory 14, and which is in-vivo information, determines whether or not medication is required for a diseased part X which is displayed in this photographic image, and a specification section (a specification device) 92 which specifies the marking M which, based upon the determination by the determination section 91, indicates the position of the diseased part X for which medication is required.

The determination section 91, along with detecting, for example, red color from the photographic image which is stored in the memory 14, compares the detected amount thereof with a threshold value which is set in advance, and, if the result of this comparison is that it is greater than or equal to this threshold value, determines that this is a hemorrhagic site (a diseased part X) for which medication is required.

Furthermore, the specification section 92 specifies a marking M which indicates the position of this diseased part X from the in-vivo information which indicates this diseased part which has been determined by the determination section 91, and the position of the marking M which has been established in correspondence with the in-vivo information which is stored in the memory 14. At this time, the specified marking M is specified by the number in order of the marking M from the oral ingestion of the capsule, for example, as the tenth such marking M.

Figure 13:
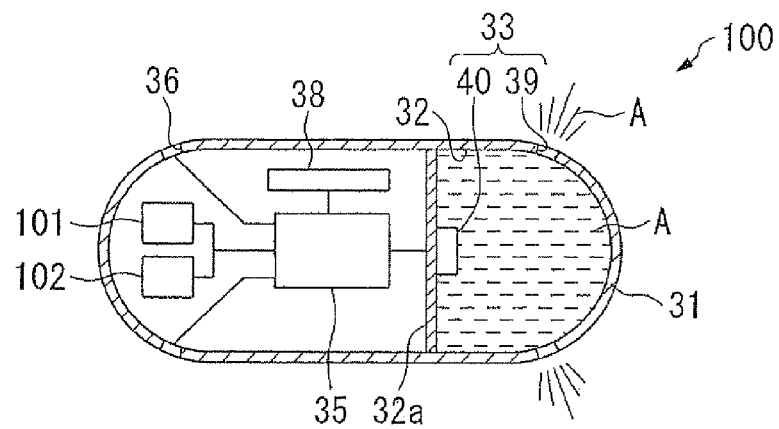
FIG. 13 is a sectional view showing a capsule for medication which is used by the capsule medication administration system shown in FIG. 11.

As shown in FIG. 13, the capsule for medication 100 includes, within a casing 31, a memory for marking (a second memory) 101 which stores information about the markings M which have been specified by the specification section 92 of the capsule for observation 90, and a decision section (a decision device) 102 which decides whether or not this marking M which has been detected by the sensors 36 is the specified marking M which is stored in the memory 101 for markings.

The decision section 102 counts the number of the markings M which are transmitted from the sensors 36, and, when it agrees with the number in order (the number) of the marking M which is stored in the memory 101 for markings, decides that this marking M which has been detected is the specified marking, and informs the control section 35. The control section 35 which receives this information causes the release device 33 to operate.

The procedure of medication with a drug A for a diseased part X within the living body P by the capsule medication administration system 80 which is structured in this manner will now be described below.

When the capsule for observation 90 which has been orally ingested by the patient P moves around within his body, along with making the markings M within the living body with the liquid chemical release device 13, acquisition of the in-vivo information, which is the photographic images, is performed by the observation device 12, and furthermore a correspondence is established by the control processing section 21 between this in-vivo information and the positions of the markings M, and is stored in the memory 14. When this has been done, the determination section 92, along with detecting only the red color from the photographic images which are stored in the memory 14, also compares the detected amount with a threshold value which is set in advance, and if it is greater than or equal to the threshold value, determines that this is a hemorrhagic site (a diseased part X) for which medication is required.

After this determination, the specification section 92 performs specification of a marking M which indicates the position of the diseased part X from the in-vivo information which indicates the diseased part X which has been determined by the determination section 91, and the position of the marking M which has been established in correspondence with the in-vivo information which is stored in the memory 14. It should be understood that, in this embodiment as well, the specified marking M is supposed to be the tenth marking M.

Next, along with retrieving the capsule for observation 90 which has been excreted from the patient P, the information about the marking M which has been specified by the specification section 92 is caused to be stored in the memory 101 for markings of the capsule for medication 100. After this, the capsule for medication 100 which has been orally ingested by the patient P performs moving within his body while detecting the markings M with the sensors 36. When the sensors 36 detect a marking M, they transmit it to the decision section 102. The decision section 102 counts the number of the markings M which are sent from the sensors 36, and performs comparison of it with the numbers of the markings M stored in the memory 101 for markings, and, when the number in order (the number) agrees, along with deciding that this marking M which has currently been detected is the specified marking, informs the control section 35 to that effect. The control section 35 which receives this information causes the heater 30 to operate, and releases the drug A from the drug aperture 39. By doing this, it is possible to perform the medication directly to the diseased part X.

Since, according to the capsule medication administration system 80 described above, the capsule for medication 100 itself decides with the decision section 102 whether or not this is the specified marking M, and performs the medication, therefore there is no requirement for any separate device for deciding upon the medication. Accordingly, it is possible to make the time which is required for release of the drug A after detection of the marking M shorter, and it is possible to release the drug A at the position of the specified marking M with high accuracy. Furthermore, this system is very simple and convenient, since there is no requirement to put on any separate device or the like.

Next, the third embodiment of the capsule medication administration system according to the present invention will be explained with reference to FIG. 14 through FIG. 18. It should be understood that in this third embodiment, to structural elements which are the same as the first embodiment, the same reference symbols are appended, and the explanation thereof is curtailed.

The point of difference between the third embodiment and the first embodiment, is the point that, whereas in the first embodiment medication was applied to the diseased part X by orally ingesting the capsule for medication 30 after the capsule for observation 10, by contrast, in the capsule medication administration system 110 of the third embodiment, after the capsule for observation 10, a capsule for long time period marking (a third capsule) 120 for long time period marking is orally ingested, and this third capsule 120 deploys a stent (a long time period marking) S, which is an indwelling member, within the living body; and, after this, a capsule for medication (a second capsule) 130 is orally ingested, and releases the drug A at the position of the stent S.

Figure 14:
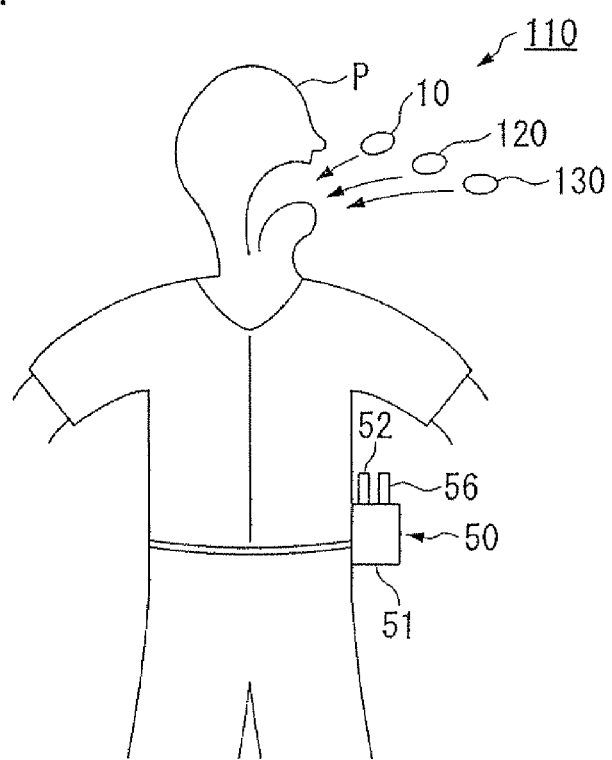
FIG. 14 is a schematic figure showing a third embodiment of the capsule medication administration system according to the present invention.

In other words, as shown in FIG. 14, the capsule medication administration system 110 of this embodiment includes the capsule for observation 10, the capsule for long time period marking 120, and the capsule for medication 130, which are orally ingested to within the living body P, and also the unit 50 external to the living body, which is fitted externally to his body.

Figure 15:
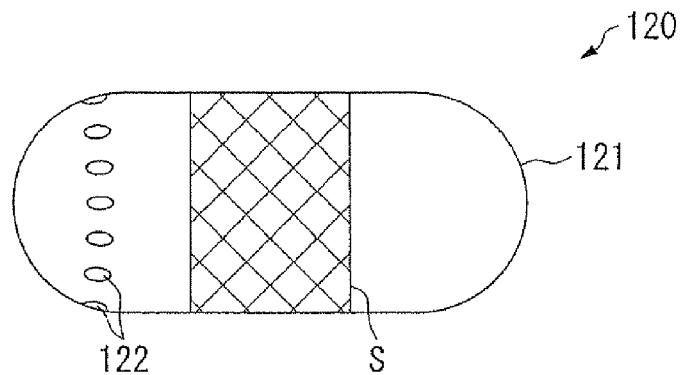
FIG. 15 is an external view showing a capsule for long time period marking which is used by the capsule medication administration system shown in FIG. 14.
Figure 16:
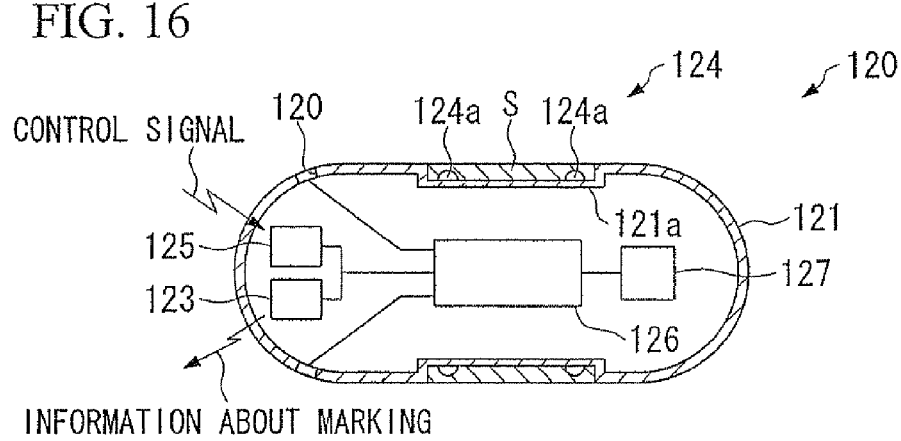
FIG. 16 is a sectional view of the capsule for long time period marking shown in FIG. 15.

As shown in FIG. 15 and FIG. 16, the capsule for long time period marking 120 includes, within a capsule shaped casing 121, sensors 122 (detection devices) which detect the markings M which have been made within the living body, a transmission antenna (a third capsule transmission device) 123 which transmits information about the markings M which has been detected by the sensors 122 to the unit 50 external to the living body, a long time period marking device 124 which includes a stent S which can last for a longer time period inside the living body than the markings M and stent release sections (implantation devices) 124a which cause deployment of this stent inside the living body, a reception antenna (a third capsule reception device) 125 which receives a control signal which has been sent and has arrived from the unit 50 external to the living body, a control section (a marking control device) 126 which causes the stent release section 124a to operate when it has received the control signal from the reception antenna 125, and a battery 127 which supplies electrical power to the various structural components described above.

The casing 121 is formed from a plastic material or the like so as tightly to seal its interior, and, at its central portion, in order to retain the stent S, there is formed a narrower diameter portion 121a whose diameter is narrower by just the amount of the thickness of the stent S. At this narrower diameter portion 121a, the stent release sections 124a are provided in plurality so as to project towards the outside. Furthermore, along with the stent S being fitted over the perimeter of the narrower diameter portion 121a so as to be wrapped around it, the stent S is retained thereupon by the stent release sections 124a. At this time, as described above, since the narrower diameter portion 121a is thinner by just the amount of the thickness of the stent S, accordingly, in the state in which the stent S is retained, the stent S does not project within the digestive organs of the living body or the like, and thus no interference occurs during moving around in the living body.

The stent S is made from a magnetic substance which has been magnetized or from a magnet or the like, and it is formed in the shape of a mesh which has a tubular form and moreover is equipped with elasticity. Furthermore, the stent S is equipped with the function of expanding in the radial direction when it is released from its state in which it is retained upon the narrower diameter portion 121a by the operation of the stent release sections 124a. Due to this, the stent S sticks fast against the lumen of the digestive organs, so as to press outwards thereupon from the inside thereof.

The sensors 122 are provided in plurality upon the outer surface of one end of the casing 121, around the axis of the casing 121. These sensors 122 are equipped with the function of detecting the markings M which have been made by the capsule for observation 10 while moving around within the living body, and of sending to the control section 126. The control section 126 sends information about the markings M which has been sent and has arrived via the transmission antenna 123 to the unit 50 external to the living body. Furthermore, when this control section 126 receives a control signal which has been sent from the unit 50 external to the living body, it releases the stent S by causing the stent release sections 124a to operate.

Figure 17:
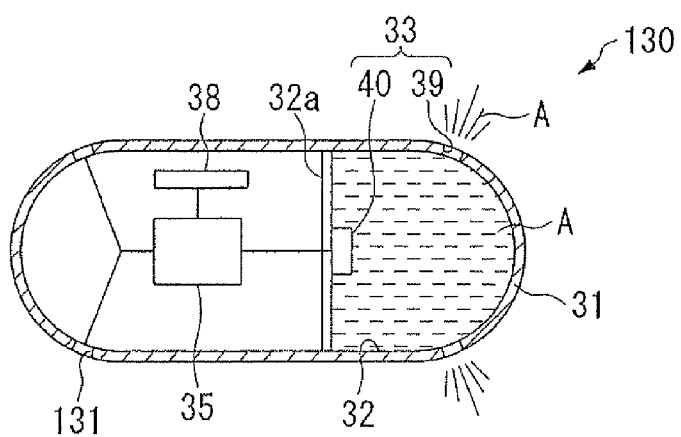
FIG. 17 is a sectional view showing a capsule for medication which is used by the capsule medication administration system shown in FIG. 14.

As shown in FIG. 17, the capsule for medication 130 includes, within a capsule shaped casing 31, a reservoir 32, a release device 33, magnetic sensors (long time period marking detection devices) 131 which detect the stent S which has been implanted by the capsule for long time period marking 120, a control section 35 which causes the release device 33 to operate when the stent S has been detected by the magnetic sensors 131, and a battery 38 which supplies electrical power to the various structural components described above.

The magnetic sensors 131 are provided in plurality upon the outer surface of the other end of the casing 31 (the opposite end thereof to the drug apertures 39), around the axis of the casing 31, and are equipped with the function of, when they have detected the stent S during moving around within the living body, notifying the control section 35 to this effect. The control section 35 which receives this notification causes the heater 40 to operate, and thereby releases the drug A within the reservoir 32 through the drug apertures 39.

Furthermore, a reception antenna 52 of the unit 50 external to the living body of this embodiment receives the information about the markings M which has been sent and has arrived from the transmission antenna 123 of the capsule for long time period marking 120, and a transmission antenna 56 transmits a control signal towards the capsule for long time period marking 120.

The case of medication with a drug A for a diseased part X in the interior of the living body P with the capsule medication administration system 110 which has the above described structure will now be explained in the following.

The capsule for observation 110 which has been orally ingested by the patient P, along with establishing a correspondence between photographic images, which are in-vivo information, and the positions of the markings M and storing the same in a memory 14, also transmits it from the transmission antenna 22 towards the unit 50 external to the living body. When this is done, the determination section 53 of the unit 50 external to the living body, along with acquiring via the reception antenna 52 this in-vivo information which is these photographic images, also, by comparing them with a threshold value, determines, for a diseased part X which is shown in the photographic images, that it is a diseased part X for which medication is required. Furthermore, from the information about the diseased part X in the living body which has been determined by the determination section 53, the specification section 54 performs specification of the marking M which is related to this in-vivo information. It should be understood that, in this embodiment as well, the specified marking M is taken as being the tenth marking M.

Furthermore, after observation by the capsule for observation 10 has been terminated by a predetermined time period elapsing from when the patient P orally ingested the capsule for observation 10, or by him excreting the capsule for observation 10, or the like, he orally ingests the capsule for long time period marking 120 according to the time period for medication which has been determined. It should be understood that, after the patient P has received the capsule for long time period marking 120 and the capsule for medication 130, he may leave the medical facility or the like.

While the capsule for long time period marking 120 which has been orally ingested is moving within the living body, the sensors 122 detect the markings M which have been made by the capsule for observation 10. When the sensors 122 detect a marking M, information about the marking M is sent to the control section 126, and the control section 126 transmits it from the transmission antenna 123 to the unit 50 external to the living body.

Figure 18:
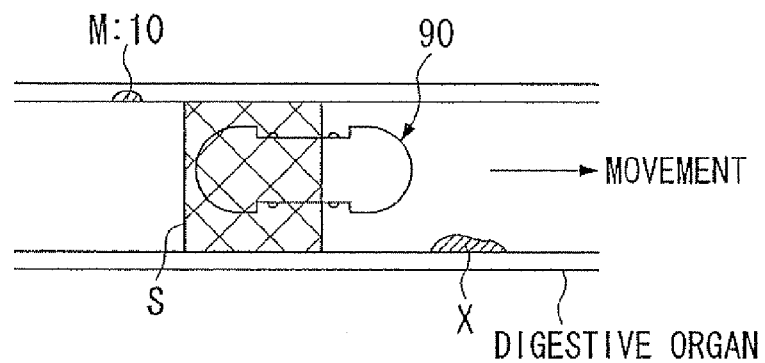
FIG. 18 is a figure showing the situation in which the capsule for long time period marking has detected a tenth marking (a specified marking) and has released a stent.

The information about the marking which has been transmitted is received by the reception antenna 52 of the unit 50 external to the living body, and it is decided by the decision section 55 whether or not it is the specified marking M. Thus, if the capsule for long time period marking 120 has detected the tenth marking M, the decision section 55, along with deciding from the count number that this is the specified marking M, also transmits a control signal from the transmission antenna 56 towards the capsule for long time period marking 120. The control signal which has been transmitted is received by the reception antenna 125 of the capsule for long time period marking 120, and is sent to the control section 126. The control section 126 receives this control signal and causes the stent release sections 124a to operate. As shown in FIG. 18, when the stent release sections 124a receive this signal from the control section 126, they release their retention of the stent S, thus releasing the stent S. The stent S which has thus been released expands in the radial direction and becomes tightly fixed by expanding and pressing against the lumen of the digestive organs. Due to this, the stent S is put into place in the vicinity of the specified marking M, and thus constitutes a sign which indicates the position of the diseased part X.

After a predetermined time period has elapsed from the oral ingestion of the capsule for long time period marking 120, or after the excretion of the capsule for long time period marking 120 or the like, the patient P orally ingests the capsule for marking 130. At this time, the patient P may take off the unit 50 external to the living body.

The capsule for medication 130 which has been orally ingested observes the interior of the living body with the magnetic sensors 131 while moving about therein. Thus, when the capsule for medication 130 arrives at the stent S, along with the magnetic sensors 131 reacting to the stent S and thereby detecting the position of the stent S, information to this effect is sent to the control section 35. The control section 35 receives this signal from the magnetic sensors 131, and causes the heater 40 to operate. Due to this, the heater 40 applies heat momentarily and causes gas bubbles to be generated, so that the thin membranes of the drug apertures 39 are broken by the pressure of these gas bubbles, whereby the drug A in the reservoir 32 is released to the exterior of the casing 31 from the drug apertures 39. At this time, since the stent S is a sign which indicates the position of the diseased part X, the drug A which has been released comes to act upon the diseased part X, and accordingly it is possible to perform medication directly upon the diseased part X.

Since, according to the capsule medication administration system 110 as described above, the stent S is implanted in the position of the specified marking M, accordingly, even if the marking M which has been made by the capsule for observation 10 is destroyed due to being metabolized, it is still possible to specify the position of the diseased part X due to its indication by the stent S.

Accordingly, even if it is necessary to perform treatment continuously over a long period of time, it is possible to apply medication easily and moreover accurately directly to the diseased part X as many times as required, simply by orally ingesting the capsule for medication 130. In particular, since the decision as to whether or not it is the specified marking is performed by the unit 50 which is external to the living body, accordingly it is possible to make the capsule 120 for long term period marking with an easy structure, and it is possible to anticipate a reduction of the size thereof.

Next, the fourth embodiment of the capsule medication administration system according to the present invention will be explained with reference to FIG. 19 and FIG. 20. It should be understood that in this fourth embodiment, to structural elements which are the same as the second embodiment, the same reference symbols are appended, and the explanation thereof is curtailed.

The point of difference between the fourth embodiment and the third embodiment, is the point that, whereas in the third embodiment, in addition to the capsule for observation 10, the capsule for long time period marking 120, and the capsule for medication 130, there was also provided the unit 50 external to the living body, by contrast, in the capsule medication administration system 140 of the fourth embodiment, the structure is one which does not incorporate any unit 50 external to the living body. It should be understood that the capsule for medication of this embodiment has the same structure as the capsule for medication 90 of the second embodiment.

Figure 19:
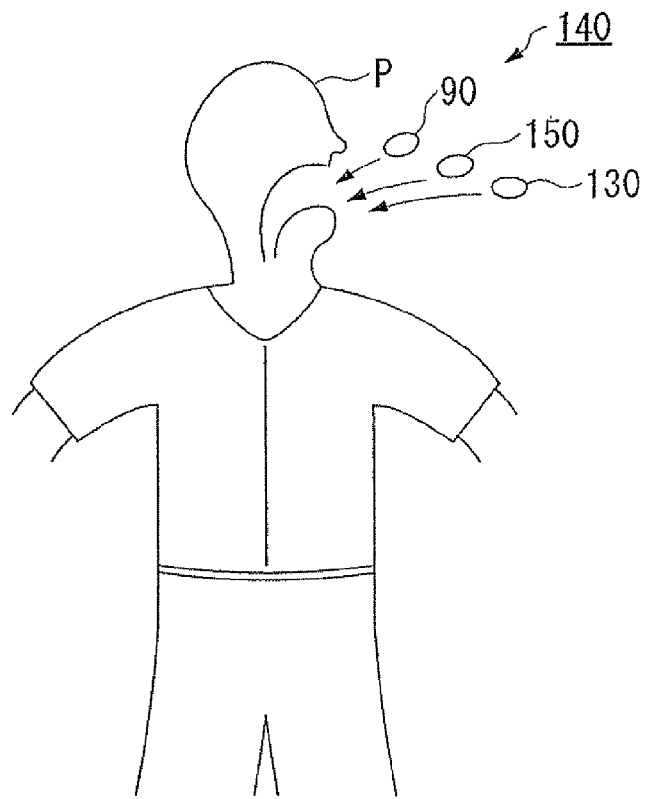
FIG. 19 is a schematic figure showing a fourth embodiment of the capsule medication administration system according to the present invention.

In other words, as shown in FIG. 19, the capsule medication administration system 140 of this embodiment includes the capsule for observation 90, the capsule for long time period marking (the third capsule) 150, and the capsule for medication 130, all of which are orally ingested into the living body.

Figure 20:
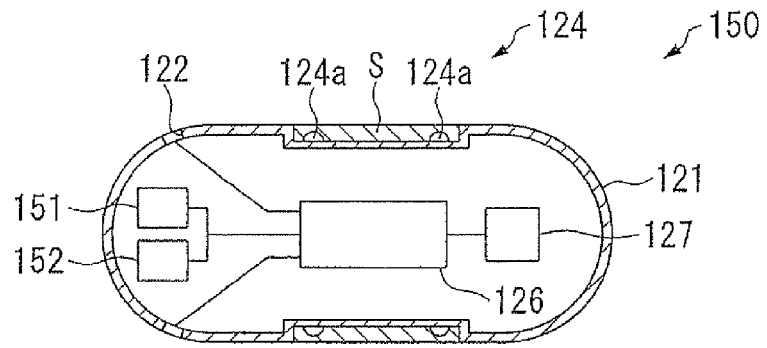
FIG. 20 is a sectional view showing a capsule for long time period marking which is used by the capsule medication administration system shown in FIG. 19.
Figure 21:
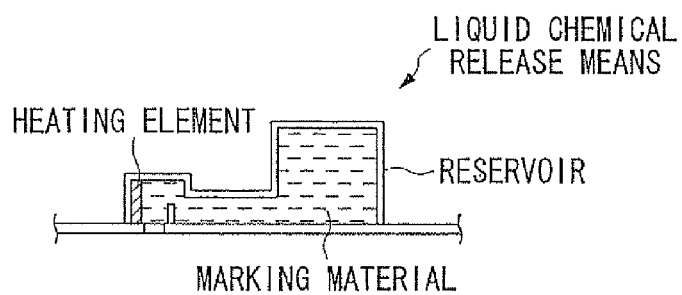
FIG. 21 is a figure showing the structure of another liquid chemical release means within the capsule for observation.

As shown in FIG. 20, the capsule for long time period marking 150 includes, within a casing 121, a memory for marking 151 which stores information about the marking M which has been specified by the specification section of the capsule for observation 90, and a decision section (a decision device) 152 which decides whether or not a marking which has been detected by the sensors 122 is the specified marking M which is stored in the memory for marking 151. Furthermore, this decision section 152 counts the number of the markings M which are sent from the sensors 122 and arrive, and, when it agrees with the number in order (the number) of the marking M which is stored in the memory for marking 151, it decides that this marking M is the specified marking M, and informs the control section 126 to this effect. Furthermore, the control section 126 which receives this notification causes the stent release section 124 to operate.

According to the capsule medication administration system 140 which has the above described type of structure, after the information about the marking M which has been specified by the specification section 92 of the capsule for observation 90 has been stored in the memory for marking 151 of the capsule for long time period marking 150, the capsule for long time period marking 150 is orally ingested. The capsule for long time period marking 150 which has been thus orally ingested, along with detecting the markings M with the sensors 122, also sends them to the decision section 152. The decision section 152 counts the number of the markings M which have been sent from the sensors 122, performs comparison of it with the number of the marking M which is stored in the memory for marking 151, and, when these numbers agree with one another, along with deciding that the marking M which has currently been detected is the specified marking M, informs the control section 126 to this effect. The control section 126 which receives this information causes the stent release sections 124 to operate and implants the stent S in the living body. Since, at this time, the capsule for long time period marking itself decides whether or not this is the specified marking and implants the stent S, accordingly it is possible to make the time period from the instant of detection which is required for the release short, and it is possible to implant the stent S in the position of the specified marling M, in other words in the position of the diseased part X, with high accuracy.

After this, release of the drug A in the position of the stent S is performed by orally ingesting the capsule for medication 130. Since at this time the stent S, as described above, indicates the position of the diseased part with high accuracy, it is possible to cause the drug A to act directly upon the diseased part X with good accuracy, and it is accordingly possible to administer medication to the diseased part X with greater accuracy. Furthermore, the entire procedure is simple and convenient, since it is not necessary for the patient to put on any separate device, or the like.

It should be understood that the field of technique of the present invention is not to be considered as being limited to the above described embodiments; it would be possible to add various alterations within its range, provided that the gist of the present invention is not departed from.

For example although, in the various embodiments described above, the decision as to whether or not it is the specified marking was made by the decision section counting the number of the markings which was sent from the capsule for observation or from the capsule for long time period marking and arrived, the present invention is not to be considered as being limited thereby. For example it would be acceptable, when making the markings within the living body, to make the markings of different shapes, sizes, colors, or the like, and to decide upon the specified marking based upon differences in these shapes or colors.

Moreover, although the determination section detects red color from the photographic image and compares it with a threshold value, the present invention is not to be considered as being limited to this; it would also be acceptable, along with paying attention to another color other than red color (blue, green, fluorescent, infra-red or the like), to apply a finite element method or the like, or to compare the detected amounts of these colors with threshold values. Moreover, it would also be acceptable to calculate the average color of the image, and to compare this average color value with a threshold value. Furthermore, it would also be acceptable not only to utilize only color, but also to extract pattern characteristics, and to make the determination based thereupon.

Yet further, it would also be acceptable to make it possible for the unit external to the living body to transmit data via the internet or the like mutually to and fro with the medical facility as well. In other words, it would be acceptable, along with transmitting the data for the in-vivo information which has been acquired to the medical facility, also to receive via data transmission information about the specified marking which has been specified by being determined by the medical facility. Since in this case the patient P would not need to visit the medical facility repeatedly, and it would be possible to administer the medication to the diseased part while he was conducting his everyday activities, accordingly it would be possible to anticipate an alleviation of the burden upon the patient. It should be understood that it would also be acceptable to arrange to set up both the medical determination device and also the specification device on the side of the medical facility.

Furthermore, although one specified marking was made, the present invention is not to be considered as being limited by this; if there were diseased part s in several locations, it would also be acceptable to arrange to medicate them when specified markings had been detected which indicated the position of each of these diseased part s. Moreover, it would also be acceptable to make specified markings before and after a diseased part, thus sandwiching it between them, and to establish the start of the medication at the initial such specified marking and the end of the medication at the next marking. By doing this, it would be possible to administer the drug to the diseased part with good efficiency, and this would also be effective if a plurality of such diseased part s were present.

Yet further, it would also be acceptable to provide a plurality of reservoirs in the capsule for medication, and to store various different types of drugs in each of these reservoirs, so as to perform medication according to the diseased part.

Moreover, although the photographic image of the living body which was formed by the observation device was used as the in-vivo information, this information is not to be considered as being limited to a photographic image. For example, it would also be acceptable for a sensor which detects pH value within the living body to be used, or a blood sensor which detects hemorrhage, or the like. In this ease, it would be possible for the presence or absence of a hemorrhage within the living body, or blood information about the quantity or component of blood or the like, to be taken as being the in-vivo information. Furthermore, it would also be acceptable to utilize an acquisition device which was made by combining a blood sensor and an observation device. By doing this, it would be possible to acquire more accurate in-vivo information.

Figure 22:
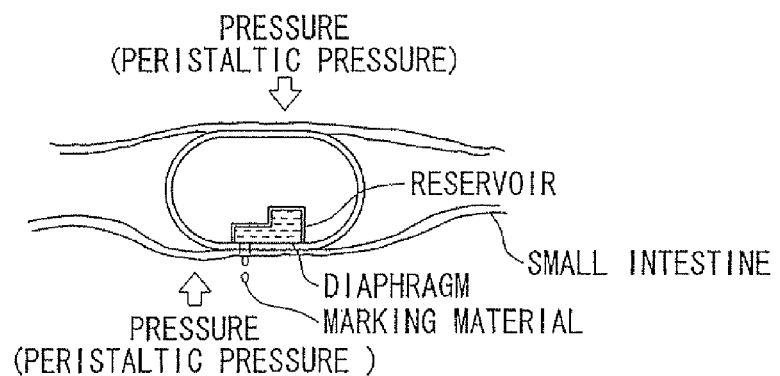
FIG. 22 is a figure showing the structure of yet another liquid chemical release means within the capsule for observation, and is a figure showing the situation in which it is positioned within the small intestine.

Furthermore although, in these embodiments, when making the markings within the living body with the capsule for observation, the marking material was discharged by a liquid chemical release device which employed a piezo element, the present invention is not to be considered as being limited thereto. For example, as shown in FIG. 22, it would also be acceptable to utilize a thermal type liquid chemical release device, in which a heating element such as a heater or the like was provided within the reservoir, and in which gas bubbles were generated by the heat of the heating element, so that the marking material was caused to be discharged by the pressure of these gas bubbles. Moreover, as shown in FIG. 23, it would also be acceptable to utilize a liquid chemical release device of a peristaltic pressure type, in which a diaphragm was provided to the reservoir, and, along with detecting the lumen pressure in the small intestine or the like, the marking material in the reservoir was caused to be discharged than in the lumen pressure.

Moreover, it would also be acceptable to employ a liquid chemical release device of the type described above in the capsule for medication, and to release the drug in the way the marking material is released. Or, it would also be acceptable to make the capsule for medication and the capsule for observation to have the same structure, and to change over the drug which is put into the reservoir according to requirements. By doing this, it would be possible to manage with only one type of capsule.

Furthermore although, in the third and the fourth embodiment, the capsule for medication detected the stent by taking advantage of a magnetic sensor, it would also be acceptable to utilize a structure in which an electromagnet was provided within the capsule, in which the drug was released by attracting the stent by taking advantage of electromagnetic force, and in which, after release, the electromagnetic force was turned off. In this manner, it would be possible to release the drug in a concentrated manner in the position of the stent more reliably.

Moreover, the long time period marking is not limited to being a stent; it would be acceptable for it to be a ring which expanded in the outward direction in the same manner, and a structure that was closed by a clip would also be acceptable. Or, one in which a magnetic substance or a radioactive substance was injected into the mucosa with an injection needle or the like would also be acceptable. In this case) the long period marking detection device might acceptably utilize a metal detection sensor or a radioactivity sensor or the like.

Yet further although, in the various embodiments described above, photographic images which have been formed of the various parts within the living body were taken as being the in-vivo information, this is not to be taken as being limitative; it would also be acceptable for this information to be continuously photographed within the living body, such as video or the like. In this case, it would be the video signal which would be stored.

Moreover, the present invention is not limited to photographing the interior of the living body by video or the like; any system will also be acceptable, provided it is one which is capable of detecting in-vivo information and of transmitting the data thereof to the device external to the living body. For example, it would be possible to utilize a capsule for checking hemorrhage which incorporated a hemoglobin sensor, or a capsule for checking information about the interior of the living body which acquired in-vivo information such as pH value, bacteria concentration, genetic abnormality and the like continuously over a long time period, or an ultrasonic wave capsule which acquired ultrasonic wave images or the like intermittently.

With the present invention, markings are made within the living body along the path of the moving of the marking device, together with the first capsule which has been orally ingested to within the living body or the like moving within the living body. After this, the detection device detects the markings which have been made by the marking device, together with the second capsule which has been orally ingested subsequent to the first capsule moving within the living body.

When the detection device detects the marking, the decision device decides whether or not this marking which has been detected is the specified marking, by comparing together the information about the marking which has been detected and the information about the marking which has been specified in advance. When the decision device decides that a marking which has been detected is the specified marking, the release control device which has received this result causes the release device to operate, and releases the drug which is retained in the drug retention section.

According to the present invention, by ensuring that the specified marking indicates the position of the diseased part, it is possible to apply the drug directly to the diseased part, and accordingly it is possible to medicate the diseased part accurately. Furthermore, since the capsule which has been ingested to within the living body does not perform the medication directly from when it has detected the diseased part, but rather performs the medication immediately that it has detected the marking which has been specified in advance, accordingly it does not happen that the capsule moves past the diseased part before the release of the drug has been performed. Furthermore, since the second capsule itself decides whether or not a marking which has been detected by the detection device is the specified marking and releases the drug, therefore no separate device or the like is required for this decision. Accordingly, it is possible to manage with only a short time period being required for releasing the drug after detection of the marking, and it is possible to perform the release of the drug at the position at which the specified marking has been made with high accuracy.

With the present invention, together with the first capsule which has been orally ingested to within the living body or the like moving within the living body, along with the in-vivo information such as images of the interior of his body being acquired by the acquisition device, also the markings are made along the path of the moving of the marking device. Based upon the in-vivo information which has been acquired by the acquisition device, the medication determination device determines whether or not medication is required for the diseased part which is indicated in the in-vivo information (for example, it may consider that hemorrhage is present when the amount of red color of the image of the interior of the living body has become greater than or equal to a threshold value, and may then decide that medication is required). When the determination that medication is required for a diseased part which is indicated in the in-vivo information has been made, the specification device receives this result and specifies the marking that has been made at the diseased part for which medication is required.

After this, together with the second capsule which has been orally ingested after the first capsule moving within the living body, the detection device detects the markings which have been made by the marking device. When the detection device detects a marking, the decision device decides whether or not this marking which has been detected is the marking which has been specified by the specification device. When the decision device decides that this marking which has been detected is the marking which has been specified by the specification device, in other words that it is the marking which has been made at the diseased part for which medication is required, then the release control device receives this result and causes the release device to operate, and releases the drug which is retained in the drug retention section.

Since, according to the present invention, the specified marking indicates the position of the diseased part, accordingly it is possible to cause the drug to act directly upon the diseased part, and it is possible to apply medication accurately to the diseased part. Furthermore, since the medication is not performed directly after the capsule which has been ingested to within the living body detects the diseased part, but rather the medication is performed directly upon detection of the specified marking which has been made in advance, accordingly it does not happen that the capsule moves past the diseased part before the drug has been completely released. Yet further, since the second capsule itself decides whether or not a marking which has been detected by the detection device is the specified marking and releases the drug, therefore no separate device or the like is required for this decision. Accordingly, it is possible to manage with only a short time period being required for releasing the drug after detection of the marking, and it is possible to perform the release of the drug at the position at which the specified marking has been made with high accuracy.

With the present invention, together with the first capsule which has been orally ingested to within the living body or the like moving within the living body, along with the in-vivo information such as images of the interior of his body being acquired by the acquisition device, also the markings are made along the path of the moving of the marking device. The in-vivo information which has been acquired by the acquisition device is stored in succession in the first memory with a correspondence being established with the positions of the markings. Based upon this in-vivo information which is stored in the first memory, the medication determination device determines whether or not medication is required for the diseased part which is indicated in the in-vivo information (for example, it may consider that hemorrhage is present when the amount of red color of the image of the interior of the living body has become greater than or equal to a threshold value, and may then decide that medication is required). When the determination that medication is required for a diseased part which is indicated in the in-vivo information has been made, the specification device specifies the marking that has been made at the diseased part for which medication is required, from among the markings which are stored in the first memory with a correspondence established with the in-vivo information. The marking which has been specified is stored in the second memory.

After this, together with the second capsule which has been orally ingested after the first capsule moving within the living body, the detection device detects the markings which have been made by the marking device. When the detection device detects a marking, the decision device decides whether or not this marling which has been detected is the marking which has been specified by the specification device, by comparing together the information about the marking which has been detected and the information about the marking which has been stored in the second memory. When the decision device decides that this marking which has been detected is the marking which has been specified by the specification device, in other words that it is the marking which has been made at the diseased part for which medication is required, then the release control device receives this result and causes the release device to operate, and releases the drug which is retained in the drug retention section.

Since, according to the present invention, the specified marking indicates the position of the diseased part, accordingly it is possible to apply the drug directly to the diseased part, and it is possible to apply medication to the diseased part more accurately. Furthermore, since the medication is not performed directly after the capsule which has been ingested to within the living body detects the diseased part, but rather the medication is performed directly upon detection of the specified marking which has been made in advance, accordingly it does not happen that the capsule moves past the diseased part before the drug has been completely released. Yet further, since the second capsule itself decides whether or not a marking which has been detected by the detection device is the specified marking and releases the drug, therefore no separate device or the like is required for this decision. Accordingly, it is possible to manage with only a short time period being required for releasing the drug after detection of the marking, and it is possible to perform the release of the drug at the position at which the specified marking has been made with high accuracy.

With the present invention, together with the first capsule which has been orally ingested to within the living body or the like moving within the living body, along with the markings being made along the path of moving of the marking device, also the acquisition device acquires the in-vivo information such as images of the interior of his body or the like while establishing a correspondence with the positions of the markings.

With the unit external to the living body which has been disposed external to the living body, the medication determination device determines whether or not medication is required for a diseased part which is indicated in the in-vivo information, based upon the in-vivo information which has been acquired by the acquisition device. It should be understood that it will be acceptable to arrange for this determination to be performed automatically by, for example, comparing a numerical value which has been obtained from the in-vivo information such as images of the interior of his body or the like with a threshold value or the like, or it will also be acceptable to arrange for it to be performed manually by a physician or the like. When it has been determined that medication is required for a diseased part which is indicated in the in-vivo information, the specification device specifies the marking which has been made at this diseased part for which medication is required, from among the markings which have been established in correspondence with the in-vivo information.

After this, together with the second capsule which has been orally ingested after the first capsule moving within the living body, the detection device detects the markings which have been made by the marking device. When the detection device detects a marking, the second capsule transmission device transmits the information about this marking to the unit external to the living body.

In the unit external to the living body, the reception device external to the living body receives the information which has been transmitted from the second capsule. When the reception device external to the living body receives the information about the marking, the decision device compares together the information about the marking which has been received by the reception device external to the living body and the information about the marking which indicates the position of the diseased part which has been specified by the specification device, and decides whether or not the marking which has been detected is the marking which has been specified by the specification device. If the decision device decides that the marking which has been detected is the marking which has been specified by the specification device, then the transmission device external to the living body transmits a control signal to the second capsule.

In the second capsule, the second capsule reception device receives the control signal which has been transmitted from the unit external to the living body. When the second capsule reception device receives this control signal, the release control device is caused to operate upon receipt of this control signal, and the drug which is being retained in the drug retention section is released.

According to the present invention, it is possible to apply the drug directly to the diseased part, and it is possible to perform medication for the diseased part more accurately. Furthermore, since the unit external to the living body includes the medication determination device which determines whether or not medication is required, the specification device which specifies the marking, and the decision device which decides upon the marking, accordingly the structures of the first capsule and of the second capsule can be made simple, and it is therefore possible to anticipate a reduction in size of both of these capsules.

With the present invention, together with the first capsule which has been orally ingested to within the living body or the like moving within the living body, along with the in-vivo information such as images of the interior of his body being acquired by the acquisition device, also the markings are made along the path of the moving of the marking device. The in-vivo information which has been acquired by the acquisition device is stored in succession in the first memory with a correspondence being established with the positions of the markings. Based upon this in-vivo information which is stored in the first memory, the medication determination device determines whether or not medication is required for the diseased part which is indicated in the in-vivo information (for example, it may consider that hemorrhage is present when the amount of red color of the image of the interior of the living body has become greater than or equal to a threshold value, and may then decide that medication is required). When the determination that medication is required for a diseased part which is indicated in the in-vivo information has been made, the specification device specifies the marking that has been made at the diseased part for which medication is required, from among the markings which are stored in the first memory with a correspondence established with the in-vivo information. The marking which has been specified is stored in the second memory.

After this, together with the third capsule which has been orally ingested after the first capsule moving within the living body, the detection device detects the markings which have been made by the marking device. When the detection device detects a marking, the decision device decides whether or not this marking which has been detected is the marking which has been specified by the specification device, by comparing together the information about the marking which has been detected and the information about the marking which has been stored in the second memory. When the decision device decides that this marking which has been detected is the marking which has been specified by the specification device, then the marking control device receives this result and causes the long time period marking device to operate, and makes the long time period marking within the living body. This long time period marking is made in the neighborhood of the marking which has been specified, in other words of the marking which has been made at the diseased part for which medication is required, and constitutes a sign which indicates the position of the diseased part.

After this, together with the second capsule which has been orally ingested after the third capsule moving within the living body, the long time period marking detection device detects the long time period marking which has been made by the long time period marking device. When the long time period marking detection device detects the long time period marking, then the release control device receives this result and causes the release device to operate, and releases the drug which is being retained in the drug retention section.

According to the present invention, by the long time period marking being maintained for a long time within the living body, the detection by the long time period marking detection device is made to be of higher accuracy. Accordingly, it is possible to administer medication to the diseased part with higher accuracy. Furthermore, since the medication is not administered directly after the capsule which has been ingested to within the living body has detected the diseased part, but rather the medication is performed immediately after detecting the long time period marking which has been made in advance, accordingly it does not happen that the capsule moves past the diseased part before completing the release of the drug. Yet further, it is possible to alleviate the burden upon the patient, even if it is necessary to perform the treatment repeatedly, since, due to the fact that the long time period marking is maintained for a long time period, it is possible to administer the medication repeatedly to the diseased part simply by orally ingesting only the second capsule.

In addition, since the third capsule itself decides whether or not a marking which has been detected by the detection device is the specified marking, and makes the long time period marking accordingly, therefore, along with it being possible to make the time period which is required from the time that the specified marking has been detected until the long time period marking has been completed shorter, also it is possible to perform the release of the drug at the position where the specified marking has been made with high accuracy.

With the present invention, together with the first capsule which has been orally ingested to within the living body or the like moving within the living body, along with the markings being made along the path of moving of the marking device, also the acquisition device acquires the in-vivo information such as images of the interior of his body or the like while establishing a correspondence with the positions of the markings.

After this, together with the third capsule which has been orally ingested after the first capsule moving within the living body, the detection device detects the markings which have been made by the marking device. When the detection device detects a marking, the third capsule transmission device transmits the information about this marking to the unit external to the living body.

In the unit external to the living body, the reception device external to the living body receives the information which has been transmitted from the third capsule. When the reception device external to the living body receives the information about the marking, the medication determination device determines whether or not medication is required for a diseased part which is indicated in the in-vivo information, based upon the in-vivo information which has been acquired by the acquisition device. It should be understood that it will be acceptable to arrange for this determination to be performed automatically by comparing a numerical value which is obtained from the in-vivo information such as images of the interior of his body or the like with a threshold value or the like, or it will also be acceptable to arrange for it to be performed manually by a physician or the like. When it has been determined that medication is required for a diseased part which is indicated in the in-vivo information, then the specification device specifies the marking which has been made at this diseased part for which medication is required, from among the markings which have been established in correspondence with the in-vivo information. When the specification device specifies the marking that has been made at the diseased part for which medication is required, then the decision device decides whether or not this marking which has been detected is the marking which has been specified, based upon the marking which has been specified by the specification device, and the information about the marking which has been received by the reception device external to the living body. When the decision device decides that the marking which has been detected is the marking which has been specified, then the transmission device external to the living body transmits a control signal to the third capsule.

In the third capsule, the third capsule reception device receives the control signal which has been transmitted from the unit external to the living body. When the third capsule reception device receives this control signal, the marking control device receives this control signal and causes the long time period marking device to operate, and makes the long time period marking within the living body. This long time period marking is made in the vicinity of the marking which has been specified, in other words of the marking which has been made at the diseased part for which medication is required, and constitutes a sign which indicates the position of the diseased part.

After this, together with the second capsule which has been orally ingested after the third capsule moving within the living body, the long time period marking detection device detects the long time period marking which has been made by the long time period marking device. When the long time period marking detection device detects the long time period marking, the release control device receives this result and causes the release device to operate, and this releases the drug which is being retained in the drug retention section.

According to the present invention, since the long time period marking maintains within the living body for a longer time period, the detection by the long time period marking detection device is made at higher accuracy. Accordingly, it is possible to administer the medication to the diseased part with higher accuracy. Furthermore, since the medication is not administered directly after the capsule which has been ingested to within the living body has detected the diseased part, but rather the medication is performed immediately after detecting the long time period marking which has been made in advance, accordingly it does not happen that the capsule moves past the diseased part before completing the release of the drug. Yet further, it is possible to alleviate the burden upon the patient, even if it is necessary to perform the treatment repeatedly, since, due to the fact that the long time period marking is maintained for a long time period, it is possible to administer the medication repeatedly to the diseased part simply by orally ingesting only the second capsule.

According to the present invention, since the third capsule itself decides whether or not a marking which has been detected by the detection device is the specified marking, and makes the long time period marking accordingly, therefore, it is possible to manage with a shorter time period which is required from the time that the specified marking has been detected until the long time period marking has been completed, it is possible to perform the release of the drug at the position where the specified marking has been made with high accuracy.

Since the unit external to the living body includes the medication determination device which determines whether or not medication is required, the specification device which specifies the marking, and the decision device which decides upon the marking, accordingly the structures of the first capsule and of the second capsule can be made simple, and it is therefore possible to anticipate a reduction in size of both of these capsules.

With the present invention, by deploying the indwelling member such as a stent or a ring or the like as the long time period marking within the living body, it is possible to make the long time period marking within the living body simply and easily.

With the present invention, together with the first capsule moving within the living body, the acquisition device acquires the in-vivo information while establishing it in correspondence with the positions of the markings. The in-vivo information which has been acquired is stored in succession in the third memory with the correspondence being established with the positions of the markings. The in-vivo information is obtained from the third memory by retrieving the first capsule which has been excreted from the living body by excretion, it is possible for the determination by the medication determination device to be performed reliably and moreover accurately.

With the present invention, as the first capsule moves within the living body, the acquisition device acquires the in-vivo information while establishing a correspondence with the positions of the markings. When the acquisition device acquires the in-vivo information, the transmission device wirelessly transmits this in-vivo information which has thus been acquired to the unit external to the living body. By doing this, it is possible for the medical determination device to acquire the in-vivo information in real time, and accordingly it is possible for a speedy determination to be performed.

Since, with the present invention, the decision device decides upon the specified marking simply according to the number of the markings which it has counted, and does not make this decision by other characteristics such as its color or its shape or the like, accordingly there is no requirement to incorporate any complicated decision circuit or the like, and it is possible to employ a simple construction. Furthermore, it is possible to enhance the reliability, since it is possible to anticipate a reduction in detection errors.

With the present invention, it is possible easily to make the markings within the living body by releasing the liquid chemical.

With the present invention, it is possible to acquire more precise images by photographing the living body when it has been illuminated with the illumination device. It is possible to take advantage of the photographic images which have been obtained by the observation device as the in-vivo information.

With the present invention, as the in-vivo information, it is possible to take advantage of blood information such as the presence or absence of blood within the living body, or the amount or the components thereof, which has been acquired by a blood sensor.

Although, in the above, preferred embodiments of the present invention have been explained, the present invention is not limited to the various embodiments described above. Within a range that does not depart from the gist of the present invention, additions, deletions, substitutions, and other changes may be made. Thus, the present invention is not limited by the previously described explanation, but is only limited by the range of the appended claims.

What is claimed is:

1. A medication administration system, comprising: a first medical device, a second medical device and a third medical device which are ingested within a living body, and a unit external to the living body which is disposed outside the living body, wherein a) the first medical device comprises: a marking device which makes markings on a body tissue of the living body; and an acquisition device which acquires in-vivo information while establishing a correspondence with the positions of the markings; b) the second medical device comprises: a drug retention section which retains a drug for administration within the living body; a release device which releases the drug retained in the drug retention section; a marking detection device which detects markings made by a marking device; and a release control device which causes the release device to operate, when the marking detection device has detected the marking; c) the third medical device comprises: a detection device which detects the markings made by the marking device; the long time period marking device which makes the long time period marking which can remain in the living body, last for a long time period within the living body than even if the marking is destroyed by being metabolized; a third medical device transmission device which transmits information regarding the markings which have been detected by the detection device towards the unit external to the living body; a third medical device reception device which receives a control signal for causing the long time period marking device to operate; and a long time period marking control device which causes the long time period marking device to operate, when the control signal has been received by the third medical device reception device; and d) the unit external to the living body comprises: a reception device external to the living body which receives the information regarding the markings which has been transmitted from the third medical device transmission device; a medication determination device which determines whether or not to administer medication for a site which is indicated in the in-vivo information based upon the in-vivo information which has been acquired by the acquisition device; a specification device which specifies a marking which indicates a site to administer medication from among the markings which have been made within the living body based on the determination by the medication determination device; a decision device for deciding whether or not a marking which has been detected by the detection device is the marking which has been specified by the specification device based on the information regarding the markings which have been received by the reception device external to the living body; and a transmission device external to the living body which transmits the control signal towards the third medical device reception device, when the decision device has decided that the marking which has been detected by the detection device is the marking which has been specified by the specification device.

2. A medication administration system according to claim 1, wherein
the first medical device further comprises a first medical device transmission device which transmits the in-vivo information which has been acquired by the acquisition device toward the unit external to the living body;
the reception device external to the living body receives the in-vivo information which has been transmitted by the first medical device transmission device; and
the medication determination device determines whether or not to administer medication for the site which is indicated in the in-vivo information based on the in-vivo information which has been received by the reception device external to the living body.

3. A medication administration system according to claim 1, wherein
the first medical device further comprises a first memory which establishes the in-vivo information which has been acquired by the acquisition device; and
the medication determination device determines whether or not to administer medication for the site which is indicated in the in-vivo information based on the in-vivo information established in the first memory.

4. A medication administration system according to claim 1, wherein each of the first and second medical devices is formed in a capsule-shape.

5. A medication administration system according to claim 1, wherein
the decision device comprises a counter for counting the number of the marking detections by the detection device, every time the detection device detects each of the markings which have been made within the living body, further wherein
the decision device decides that the marking which is detected by the detection device is the specified marking, when the number of the marking arrives a specified number.

6. A medication administration system according to claim 1, wherein the marking device comprises a liquid chemical release device which releases a liquid chemical within the living body.

7. A capsule medication administration system according to claim 1, wherein the acquisition device comprises an observation device, the observation device has an imaging device which forms an image of the interior of the living body and an illumination device which illuminates the interior of the living body.

8. A medication administration system according to claim 1, wherein the acquisition device comprises a blood sensor which detects hemorrhage within the living body.

9. A medication administration system, comprising: a first medical device, a second medical device and a third medical device which are ingested within a living body, wherein a) the first medical device comprises: a marking device which makes markings on a body tissue of the living body; and an acquisition device which acquires in-vivo information while establishing a correspondence with the positions of the markings; a medication determination device which determines whether or not to administer medication for a site which is indicated in the in-vivo information based upon the in-vivo information which has been acquired by the acquisition device; and a specification device which specifies a marking which indicates a site to administer medication from among the markings which have been made within the living body based on the determination by the medication determination device; b) the second medical device comprises: a drug retention section which retains a drug for administration within the living body; a release device which releases the drug retained in the drug retention section; a marking detection device which detects a marking made by a marking device; and a release control device which causes the release device to operate, when the marking detection device has detected the marking; c) the third medical device comprises: a detection device which detects the markings made by the marking device; the marking device which makes the marking which can remain in the living body last if the marking is destroyed by being metabolized; a third memory which establishes an information which has been specified by the specification device; a decision device for deciding whether or not a marking which has been detected by the detection device is the marking which has been specified by the specification device based on the information regarding the markings established by the third memory; and a marking control device which causes the marking device to operate, when the decision device has decided that the marking which has been detected by the detection device is the marking which has been specified by the specification device.

10. A medication administration system according to claim 9, wherein each of the first and second medical devices is formed in a capsule-shape.

11. A medication administration system according to claim 9, wherein the decision device comprises a counter for counting the number of the marking detections by the detection device, every time the detection device detects each of the markings which have been made within the living body, further wherein the decision device decides that the marking which is detected by the detection device is the specified marking, when the number of the marking arrives a specified number.

12. A medication administration system according to claim 9, wherein the marking device comprises a liquid chemical release device which releases a liquid chemical within the living body.

13. A medication administration system according to claim 9, wherein the acquisition device comprises an observation device, the observation device has an imaging device which forms an image of the interior of the living body and an illumination device which illuminates the interior of the living body.

14. A medication administration system according to claim 9, wherein the acquisition device comprises a blood sensor which detects hemorrhage within the living body.

* * * * *